(12) United States Patent
Rondeau

(10) Patent No.: US 7,485,157 B2
(45) Date of Patent: Feb. 3, 2009

(54) DYE COMPOSITION FOR KERATIN FIBERS, WITH A CATIONIC DIRECT DYE AND A SUBSTANTIVE POLYMER

(75) Inventor: Christine Rondeau, Sartrouville (FR)

(73) Assignee: Loreal, Paris (FR)

( * ) Notice: Subject to any disclaimer, the term of this patent is extended or adjusted under 35 U.S.C. 154(b) by 0 days.

(21) Appl. No.: 11/727,834

(22) Filed: Mar. 28, 2007

(65) Prior Publication Data

US 2008/0078036 A1    Apr. 3, 2008

Related U.S. Application Data

(63) Continuation of application No. 10/761,213, filed on Jan. 22, 2004, now abandoned, which is a continuation of application No. 09/287,176, filed on Apr. 6, 1999, now abandoned.

(30) Foreign Application Priority Data

Apr. 6, 1998    (FR) .................... 98 04234

(51) Int. Cl.
*A61Q 5/10*    (2006.01)
(52) U.S. Cl. ............... 8/405; 8/406; 8/407; 8/410; 8/411; 8/426; 8/552; 8/554
(58) Field of Classification Search .......... 8/405, 8/406, 407, 410, 411, 426, 435, 552, 554
See application file for complete search history.

(56) References Cited

U.S. PATENT DOCUMENTS

| | | | |
|---|---|---|---|
| 3,869,454 A | 3/1975 | Lang et al. |
| 3,955,918 A | 5/1976 | Lang |
| 3,985,499 A | 10/1976 | Lang et al. |
| 3,986,825 A | 10/1976 | Sokol |
| 4,025,301 A | 5/1977 | Lang |
| 4,151,162 A | 4/1979 | Lang et al. |
| 4,157,388 A | 6/1979 | Christiansen |
| 4,390,689 A | 6/1983 | Jacquet et al. |
| 4,702,906 A | 10/1987 | Jacquet et al. |
| 4,719,282 A | 1/1988 | Nadolsky et al. |
| 4,772,462 A | 9/1988 | Boothe et al. |
| 4,781,723 A | 11/1988 | Gross et al. |
| 5,393,305 A | 2/1995 | Cohen et al. |
| 5,422,031 A | 6/1995 | Nomura et al. |
| 5,735,908 A | 4/1998 | Cotteret et al. |
| 5,879,412 A | 3/1999 | Rondeau et al. |
| 5,919,273 A | 7/1999 | Rondeau et al. |
| 5,948,124 A | 9/1999 | Grit |
| 5,993,490 A | 11/1999 | Rondeau et al. |
| 6,001,135 A | 12/1999 | Rondeau et al. |
| 6,007,585 A | 12/1999 | Syed et al. |

FOREIGN PATENT DOCUMENTS

| | | |
|---|---|---|
| DE | 44 21 031 | 12/1995 |
| DE | 295 12 302 | 1/1997 |
| EP | 0 132 960 | 2/1985 |
| EP | 0 189 935 | 8/1986 |
| EP | 0 557 203 | 8/1993 |
| EP | 0 367 926 | 10/1993 |
| EP | 0 673 641 | 2/1995 |
| EP | 0 714 954 | 6/1996 |
| EP | 0 756 861 | 7/1996 |
| EP | 0 850 638 | 7/1998 |
| FR | 2 270 846 | 12/1975 |
| FR | 2 282 860 | 3/1976 |
| FR | 2 586 913 | 3/1987 |
| WO | WO 95/01772 | 1/1995 |
| WO | WO 95/15144 | 6/1995 |
| WO | WO 97/39727 | 10/1997 |

OTHER PUBLICATIONS

Richard J. Crawford et al., "A replacement of Rubine dye for detecting cationics on keratin", Journal of the Society of Cosmetic Chemist, vol. 31, No. 2, Mar./Apr. 1980, pp. 274-278.
English language Derwent Abstract of DE 44 21 031, (1995).
English language Derwent Abstract of DE 295 12 302, (1997).
English language Derwent Abstract of EP 0 557 203, (1993).
English language Derwent Abstract EP 0714 954, (1996).
English language Derwent Abstract EP 0 367 926, (1993).
English language Derwent Abstract of EP 0 673 641, (1995).
English language Derwent Abstract EP 0850 638, (1998).
English language Dewent Abstract of FR 2 270 846, (1975).
English language Derwent abstract of FR 2 586 913, (1987).
Technical Report of Experimental Test carried out for European Appeal Proceedings (No date).*

* cited by examiner

*Primary Examiner*—Eisa B Elhilo
(74) *Attorney, Agent, or Firm*—Finnegan, Henderson, Farabow, Garrett & Dunner, L.L.P.

(57) ABSTRACT

The invention relates to a dye composition for keratin fibers, in particular for human keratin fibers such as the hair, this composition having, in a medium suitable for dyeing, at least one cationic direct dye of given formula, and containing at least one specific cationic or amphoteric substantive polymer. The invention also relates to the dyeing processes and devices using it.

40 Claims, No Drawings

DYE COMPOSITION FOR KERATIN FIBERS, WITH A CATIONIC DIRECT DYE AND A SUBSTANTIVE POLYMER

CROSS-REFERENCE TO RELATED APPLICATIONS

This is a continuation of application Ser. No. 10/761,213, filed Jan. 22, 2004, abandoned which is a continuation of application Ser. No. 09/287,176 filed Apr. 6, 1999, abandoned the disclosure of which is incorporated herein by reference.

FIELD OF THE INVENTION

The invention relates to a dye composition for keratin fibers, especially human keratin fibers, such as the hair, this composition comprising, in a medium suitable for dyeing, at least one cationic direct dye of the below given formulae and at least one specific cationic or amphoteric substantive polymer.

The invention also relates to the dyeing processes and devices using this composition.

BACKGROUND OF THE INVENTION

Two types of dyeing can be distinguished in the hair sector. The first type of dyeing is semi-permanent or temporary dyeing, also known as direct dyeing, which uses dyes capable of giving the hair's natural coloration a more or less pronounced color change that may be resistant to several shampoo-washes. These dyes are known as direct dyes; they can be used with or without an oxidizing agent. In the presence of an oxidizing agent, the aim is to effect a lightening dyeing. The lightening dyeing is carried out by applying the mixture, prepared at the time of use, of a direct dye and of an oxidizing agent to the hair, and obtains, by lightening the melanin in the hair, an advantageous effect, such as unifying the color in the case of grey hair, or bringing out the color in the case of naturally pigmented hair.

The second type of dyeing is permanent dyeing or oxidation dyeing. This type of dyeing is carried out with so-called "oxidation" dyes comprising oxidation dye precursors and couplers. Oxidation dye precursors, commonly referred to as "oxidation bases," are compounds that are initially colorless or only weakly colored, and that develop their dyeing power on the hair in the presence of oxidizing agents added at the time of use, leading to the formation of colored compounds and dyes. The formation of these colored compounds and dyes results either from an oxidative condensation of the "oxidation bases" with themselves, or from an oxidative condensation of the "oxidation bases" with coloration modifier compounds, commonly known as "couplers," which are generally present in the dye compositions used in oxidation dyeing.

To vary the shades obtained with oxidation dyes, or to enrich them with glints, it is known practice to add direct dyes thereto.

Among the cationic direct dyes available in the field of dyeing keratin fibers, especially human keratin fibers, the compounds whose structure is developed in the following text are already known; however, these dyes lead to insufficient colorations, both regarding the homogeneity of the color distributed along the fiber ("unison"), where the coloration is said to be too selective, and regarding the staying power, where the hair resists various attacking factors, including light, bad weather, and shampooing.

SUMMARY OF THE INVENTION

Now, after considerable research conducted in this area, the Inventor has discovered that it is possible to obtain novel compositions for dyeing keratin fibers capable of giving colorations that are less selective and that show good resistance to the various attacking factors to the hair, by combining at least one specific cationic or amphoteric substantive polymer with at least one cationic direct dye known in the art and of formulae respectively defined below.

This discovery forms the basis of the present invention.

Additional features and advantages of the invention are set forth in the description that follows, and, in part, will be apparent from the description or may be learned from practice of the invention. The advantages of the invention will be realized and attained by the dyeing compositions, processes, and kits particularly pointed out in the written description and claims.

Both the foregoing general description and the following detailed description of the invention are exemplary and explanatory only and are not restrictive of the claimed invention.

DETAILED DESCRIPTION OF THE INVENTION

A first subject of the present invention is thus a composition for dyeing keratin fibers, and especially human keratin fibers, such as the hair, which composition comprises, in a medium suitable for dyeing, (i) at least one cationic direct dye whose structure corresponds to the following formulae, and (ii) at least one specific cationic or amphoteric substantive polymer.

(i) The cationic direct dye which can be used according to the present invention is a compound selected from those of formulae (I), (II), (III) and (III') below:

a) the compounds of formula (I) below:

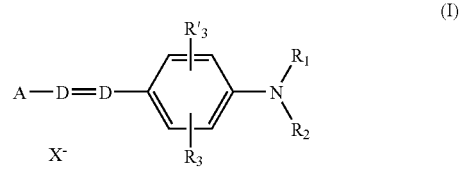

wherein:

D represents a nitrogen atom or a —CH group;

$R_1$ and $R_2$ are identical or different and represent a hydrogen atom, a $C_1$-$C_4$ alkyl radical which is unsubstituted or substituted with a —CN, —OH or —$NH_2$ radical, or $R_1$ and $R_2$ form, with a carbon atom of the benzene ring, an optionally oxygenated or nitrogenous heterocycle which is unsubstituted or substituted with one or more $C_1$-$C_4$ alkyl radicals, or $R_1$ and $R_2$ may each be a 4'-aminophenyl radical;

$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;

$X^-$ represents an anion preferably selected from chloride, methyl sulphate and acetate;

A represents a group selected from structures A1 to A19 below:

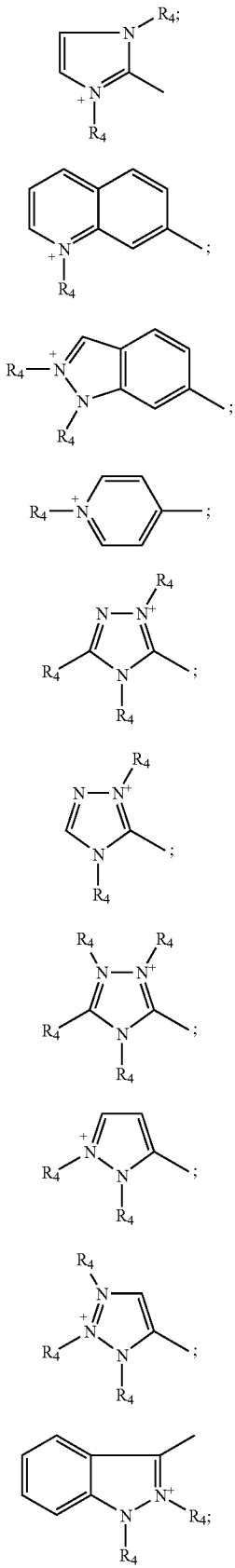
wherein $R_4$ represents a $C_1$-$C_4$ alkyl radical which is unsubstituted or substituted with a hydroxyl radical and $R_5$ represents a $C_1$-$C_4$ alkoxy radical,
with the proviso that when D represents —CH, and A represents $A_4$ or $A_{13}$ and $R_3$ is other than an alkoxy radical, then $R_1$ and $R_2$ do not simultaneously represent a hydrogen atom;

b) the compounds of formula (II) below:

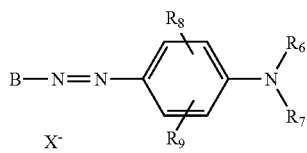

(II)

wherein:
$R_6$ represents a hydrogen atom or a $C_1$-$C_4$ alkyl radical;
$R_7$ represents a hydrogen atom, an alkyl radical which is unsubstituted or substituted with a —CN radical or with an amino group, a 4'-aminophenyl radical, or forms, with $R_6$, an optionally oxygenated and/or nitrogenous heterocycle which is unsubstituted or substituted with a $C_1$-$C_4$ alkyl radical;
$R_8$ and $R_9$ are identical or different and represent a hydrogen atom, a halogen atom such as bromine, chlorine, iodine or fluorine, a $C_1$-$C_4$ alkyl or $C_1$-$C_4$ alkoxy radical or a —CN radical;
$X^-$ represents an anion, preferably selected from chloride, methyl sulphate and acetate;
B represents a group selected from structures B1 to B6 below:

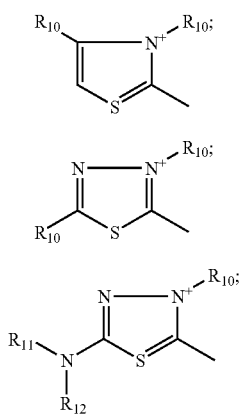

B1

B2

B3

B4

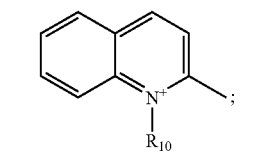

B5

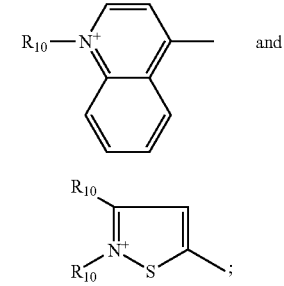

and

B6

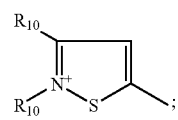

wherein $R_{10}$ represents a $C_1$-$C_4$ alkyl radical; $R_{11}$ and $R_{12}$ are identical or different, represent a hydrogen atom or a $C_1$-$C_4$ alkyl radical;

c) the compounds of formulae (III) and (III') below:

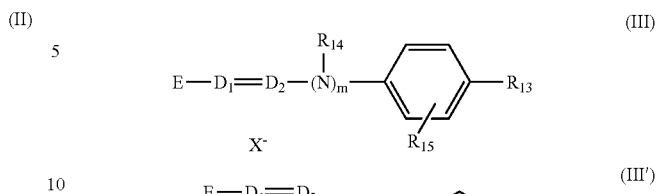

(III)

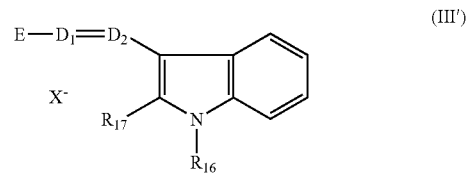

(III')

wherein:
$R_{13}$ represents a hydrogen atom, a $C_1$-$C_4$ alkoxy radical, a halogen atom, such as bromine, chlorine, iodine or fluorine, or an amino radical;
$R_{14}$ represents a hydrogen atom, a $C_1$-$C_4$ alkyl radical, or forms, with a carbon atom of the benzene ring, a heterocycle which is optionally oxygenated and/or substituted with one or more $C_1$-$C_4$ alkyl groups;
$R_{15}$ represents a hydrogen atom or a halogen atom such as bromine, chlorine, iodine or fluorine;
$R_{16}$ and $R_{17}$ are identical or different and represent a hydrogen atom or a $C_1$-$C_4$ alkyl radical;
$D_1$ and $D_2$ are identical or different and represent a nitrogen atom or a —CH group;
m=0 or 1;
with the proviso that when $R_{13}$ represents an unsubstituted amino group, then $D_1$ and $D_2$ simultaneously represent a —CH group and m=0;
$X^-$ represents an anion, preferably selected from chloride, methyl sulphate and acetate; and
E represents a group selected from structures E1 to E8 below:

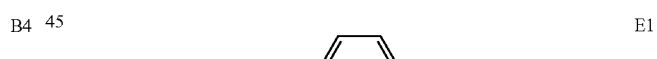

E1

E2

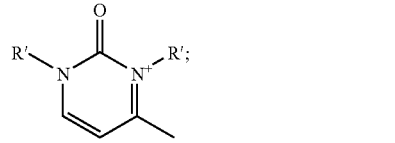

E3

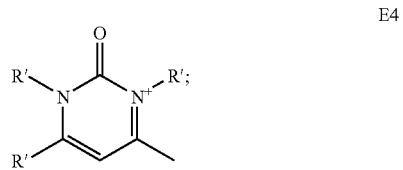

E4

-continued

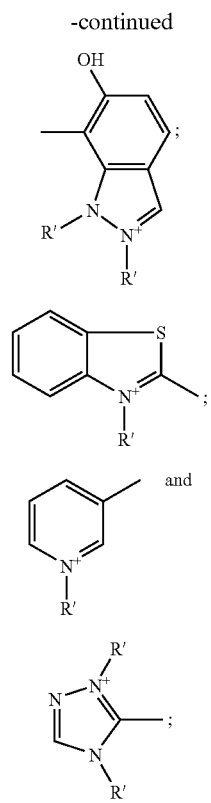

wherein R' represents a $C_1$-$C_4$ alkyl radical;

with the proviso that when m=0 and $D_1$ represents a nitrogen atom, then E can also represent a group of structure E9 below:

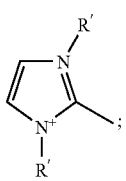

wherein R' represents a $C_1$-$C_4$ alkyl radical.

The cationic direct dyes of formulae (I), (II), (III) and (III') that can be used in the dye compositions in accordance with the invention are known compounds and are described, for example, in patent applications WO 95/01772, WO 95/15144 and EP-A-0,714,954.

The preferred cationic direct dyes of formula (I) that can be used in the dye compositions in accordance with the invention include the compounds corresponding to structures (I1) to (I55) below:

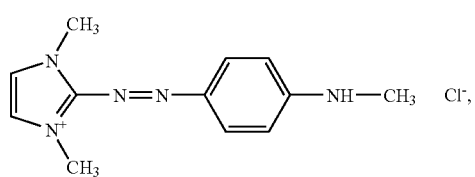

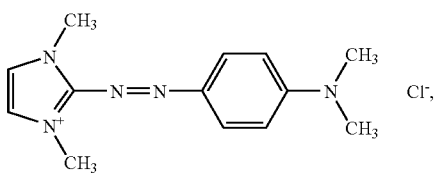

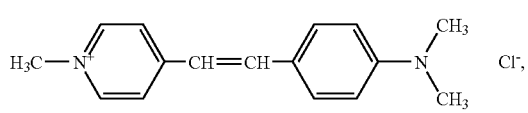

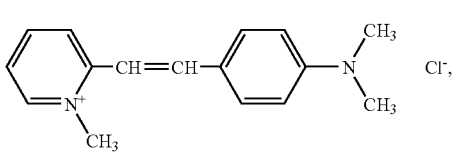

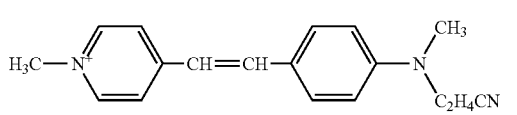

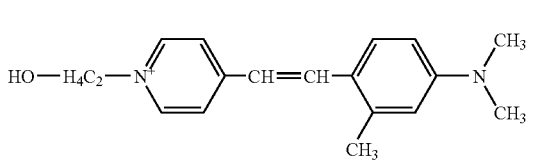

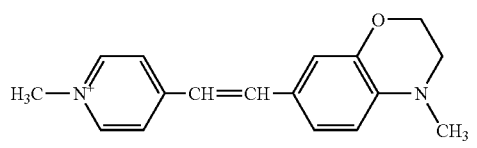

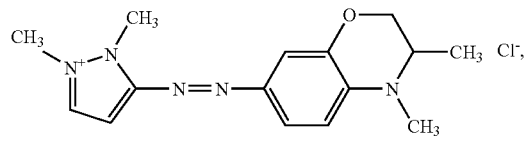

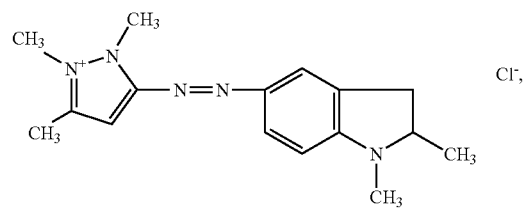

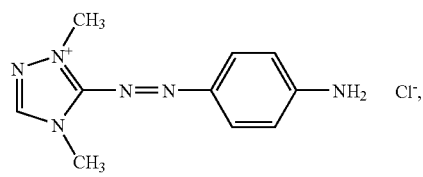

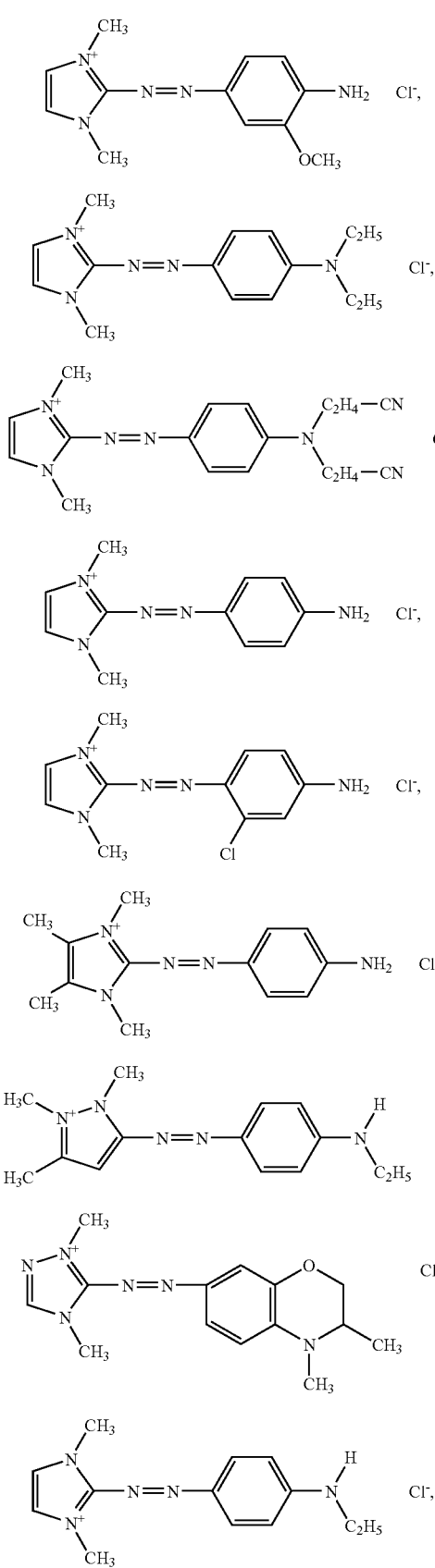
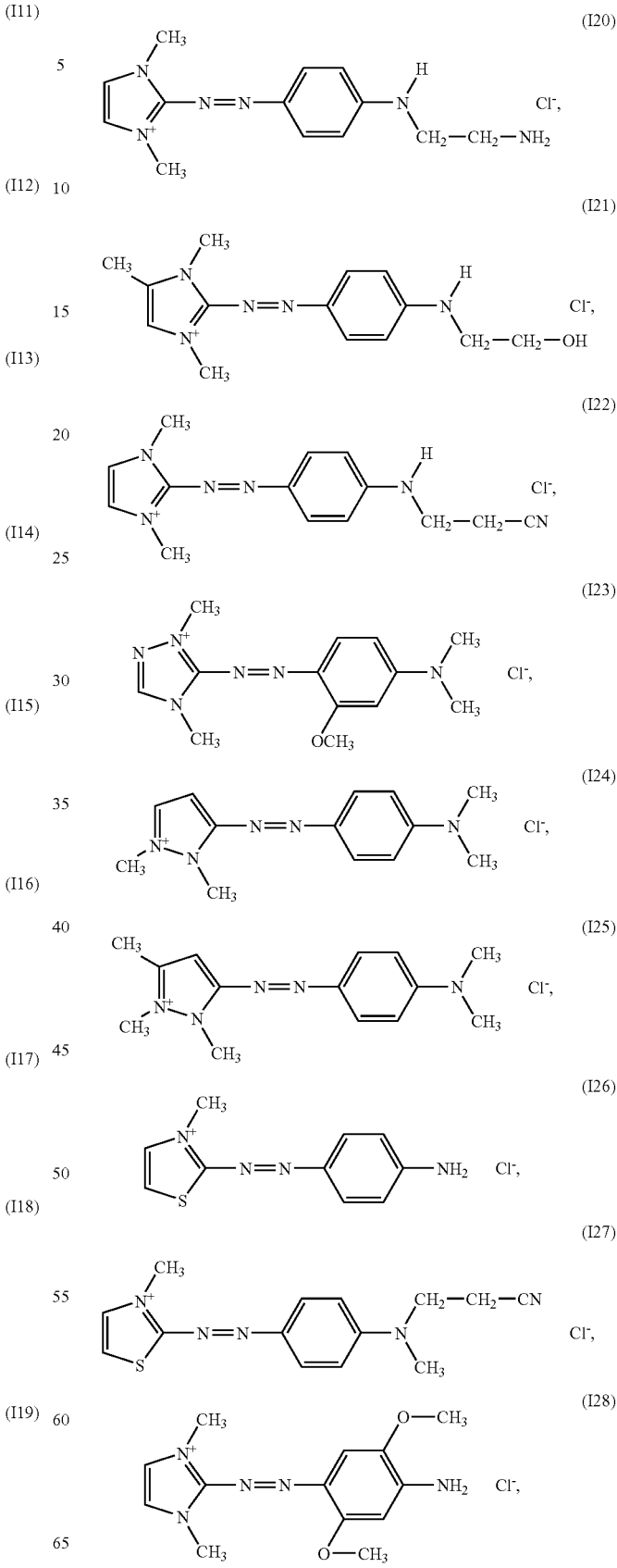

-continued (I29), (I30), (I31), (I32), (I33), (I34), (I35), (I36), (I37), (I38), (I39), (I40), (I41), (I42), (I43), (I44), (I45), (I46)

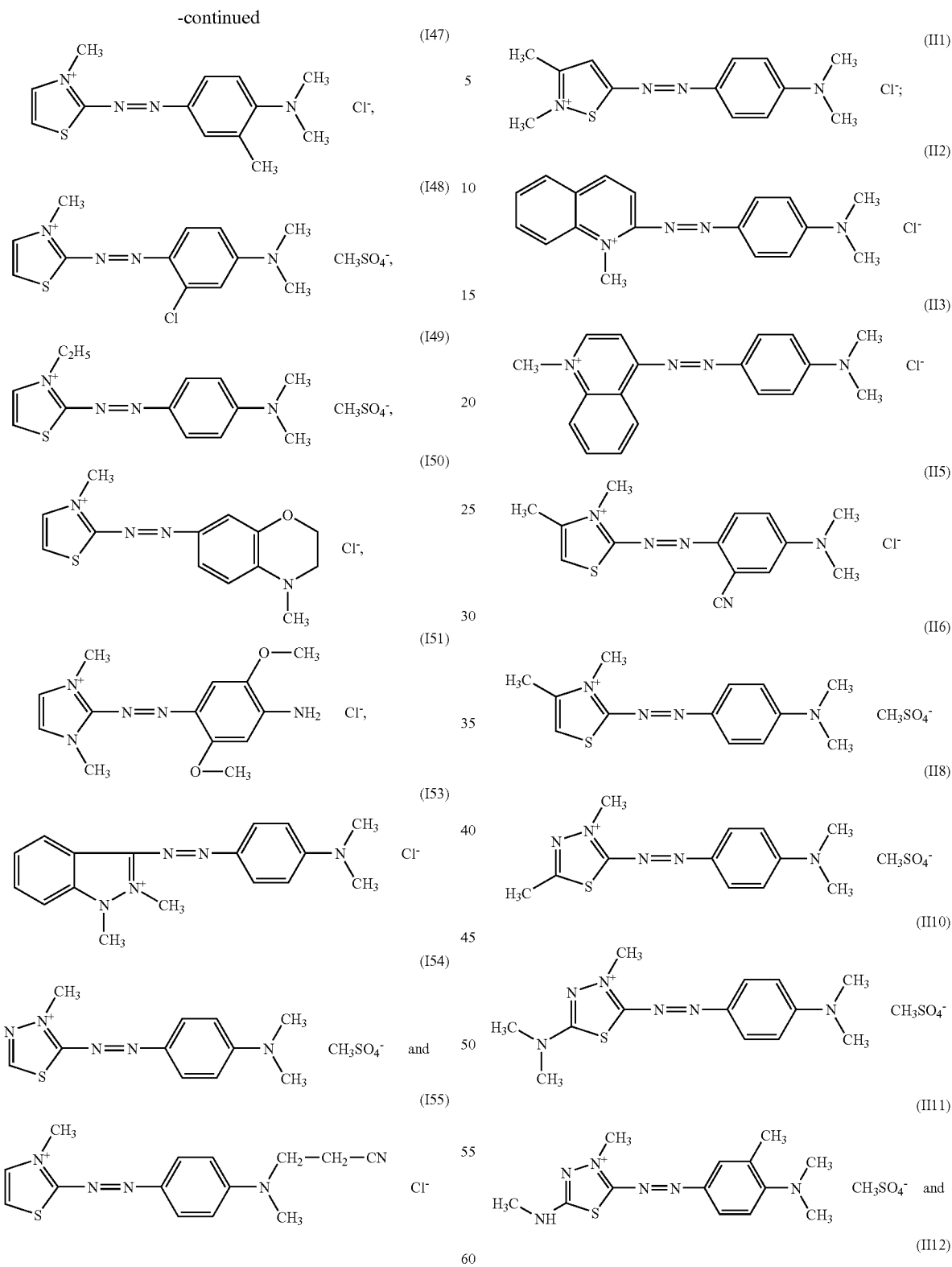
Among the compounds of structures (I1) to (I55) described above, those most preferred compounds include those corresponding to structures (I1), (I2), (I14) and (I31).
The preferred cationic direct dyes of formula (II) that can be used in the dye compositions in accordance with the invention, include the compounds corresponding to structures (II1) to (II12) below:

The preferred cationic direct dyes of formula (III) that can be used in the dye compositions in accordance with the invention, include the compounds corresponding to structures (III1) to (III18) below:
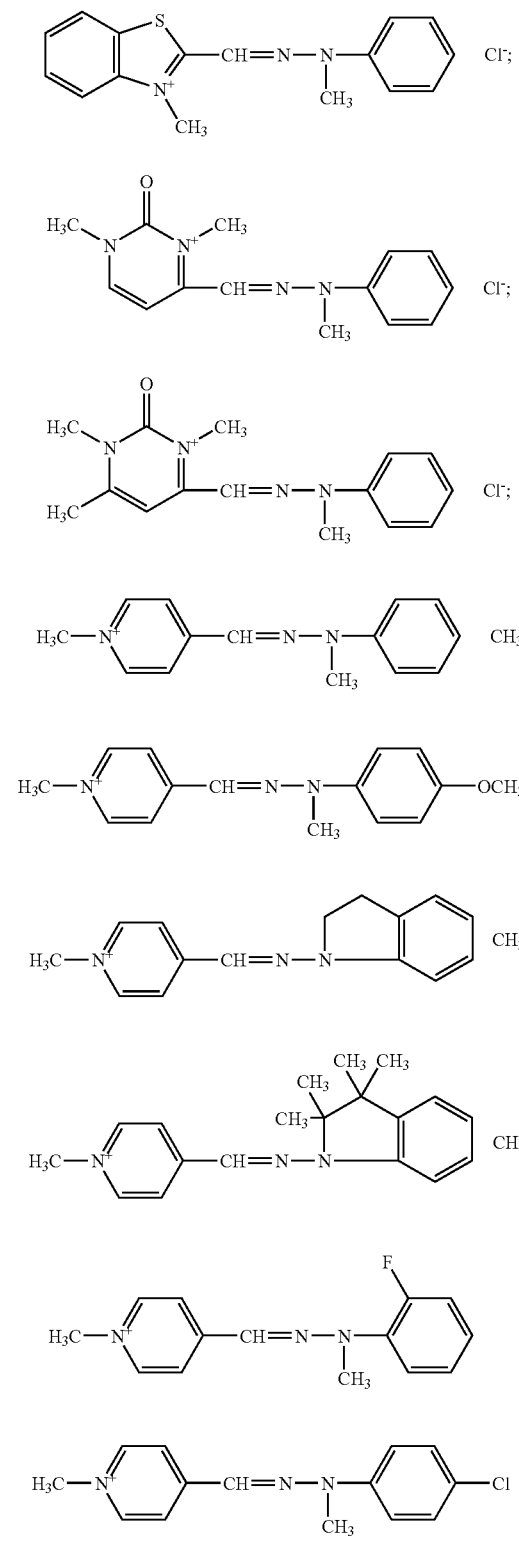
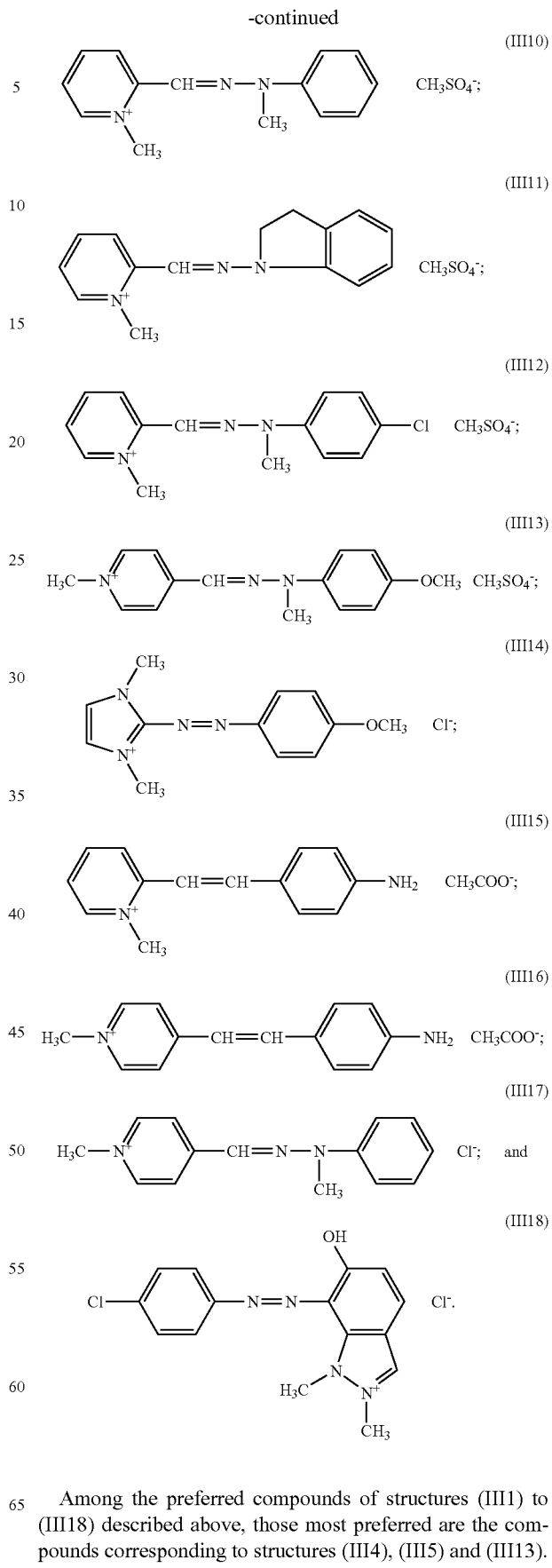
Among the preferred compounds of structures (III1) to (III18) described above, those most preferred are the compounds corresponding to structures (III4), (III5) and (III13).

The preferred cationic direct dyes of formula (III') that can be used in the dye compositions in accordance with the invention, include the compounds corresponding to structures (III'1) to (III'3) below:

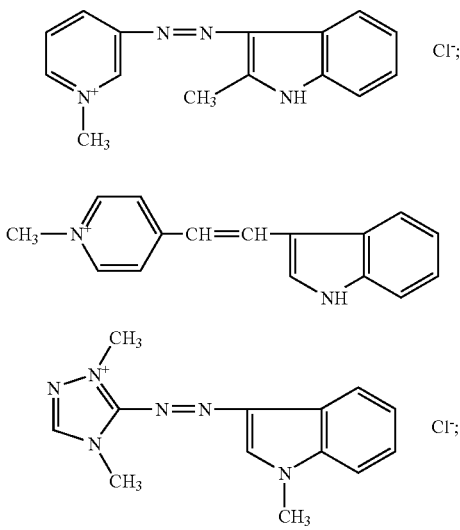

The at least one cationic direct dye used according to the invention preferably is present in amount ranging from about 0.001 to about 10% by weight relative to the total weight of the dye composition, and even more preferably from about 0.005 to about 5% by weight relative to this weight.

(ii) The cationic or amphoteric substantive polymer that can be used according to the present invention is selected from:

(a) cellulosic cationic derivatives, with the exception of Polyquaternium 10;
(b) copolymers of dimethyldiallylammonium halide and of (meth)acrylic acid;
(c) methacryloyloxyethyltrimethylammonium halide homopolymers and copolymers;
(d) polyquaternary ammonium polymers selected from:
polymers comprising repeating units corresponding to formula (IV) below:

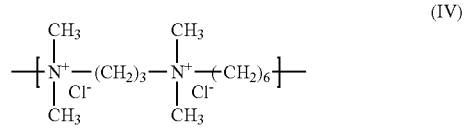

polymers comprising repeating units corresponding to formula (V) below:

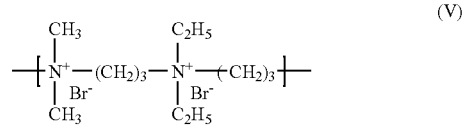

and polymers comprising repeating units corresponding to formula (VI) below:

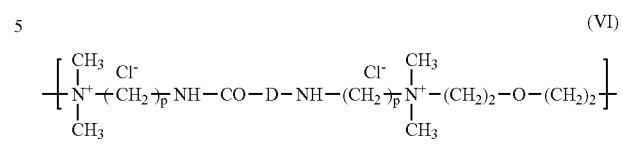

in which p represents an integer ranging from 1 to 6 approximately, D can be zero or can represent a group —$(CH_2)_r$—CO— in which r represents a number equal to 4 or 7;

(e) vinylpyrrolidone copolymers containing cationic units; and
(f) mixtures thereof.

The substantive nature, i.e., the ability to be deposited on the hair, of the polymers used in the present invention is conventionally determined using the test described by Richard J. Crawford, Journal of the Society of Cosmetic Chemists, 1980, 31-(5)-pages 273 to 278 (development with Red 80 acidic dye).

These substantive polymers can be selected from those previously described in the literature, especially in European patent application EP-A-0,557,203, from page 4, line 19 to page 12, line 14.

Preferred cationic cellulosic derivatives include quaternized cellulose ether derivatives such as those described in European patent application EP-A-0,189,935, and in particular the polymer sold under the name "Quatrisoft LM 200" by the company Union Carbide. These polymers are also defined in the CTFA dictionary (5th edition, 1993) as quaternary ammoniums of hydroxyethylcellulose that have reacted with an epoxide substituted with a lauryldimethylammonium group, and are listed therein under the name "Polyquaternium 24".

Preferred substantive polymers of the methacryloyloxyethyltrimethylammonium halide homopolymer and copolymer type that can be used according to the invention, include the products that are referred to in the CTFA dictionary (5th Edition, 1993) as (1) "Polyquaternium 37", (2) "Polyquaternium 32" and (3) "Polyquaternium 35", and which correspond (1) to crosslinked poly(methacryloyloxyethyltri-methylammonium chloride) homopolymer, as a 50% dispersion in mineral oil, sold under the name Salcare SC95 by the company Allied Colloids, (2) to the crosslinked copolymer of acrylamide and of methacryloyloxyethyltrimethylammonium chloride (20/80 by weight), as a 50% dispersion in mineral oil, sold under the name Salcare SC92 by the company Allied Colloids, and (3) to the methosulphate of the copolymer of methacryloyloxyethyltrimethylammonium and of methacryloyloxyethyldimethylacetylammonium, sold under the name Plex 7525L by the company Rohm GmbH.

The preferred substantive polymers of the copolymer of dimethyldiallylammonium halide and of (meth)acrylic acid type that can be used according to the invention, include the copolymers of diallyldimethylammonium chloride and of acrylic acid, such as the one in proportions (80/20 by weight) sold under the name Merquat 280 by the company Calgon.

The preferred substantive polymers of the polyquaternary ammonium type which can be used according to the invention, include:
the polymers prepared and described in French Patent No. 2,270,846, comprising repeating units corresponding to formula (IV) below:

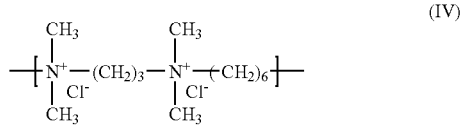

and especially those in which the molecular weight, determined by gel permeation chromatography, ranges from 9500 to 9900;

the polymers prepared and described in French Patent No. 2,270,846, comprising repeating units corresponding to formula (V) below:

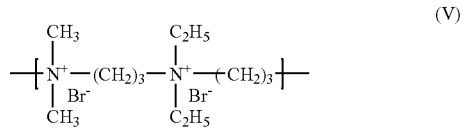

and especially those in which the molecular weight, determined by gel permeation chromatography, is about 1200;

the polymers described and prepared in U.S. Pat. Nos. 4,157,388, 4,390,689, 4,702,906 and 4,719,282, comprising repeating units corresponding to formula (VI) below:

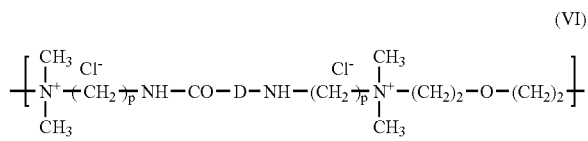

wherein p represents an integer ranging from 1 to 6 approximately, D can be zero or can represent a group —$(CH_2)_r$—CO—, further wherein r represents a number equal to 4 or 7, and wherein the molecular mass of said polymers is preferably less than 100,000, and even more preferably less than or equal to 50,000. Such polymers are sold, for example, by the company Miranol under the names "Mirapol A15", "Mirapol AD1" "Mirapol AZ1" and "Mirapol 175".

The preferred vinylpyrrolidone polymers (PVP) containing cationic units that can be used in accordance with the invention, include:

a) vinylpyrrolidone polymers containing dimethylaminoethyl methacrylate units; for example:
the vinylpyrrolidone/dimethylaminoethyl methacrylate (20/80 by weight) copolymer sold under the trade name Copolymer 845 by the company ISP,
the vinylpyrrolidone/dimethylaminoethyl methacrylate copolymers quaternized with diethyl sulphate, sold under the names Gafquat 734, 755, 755 S and 755 L by the company ISP,
the PVP/dimethylaminoethyl methacrylate/hydrophilic polyurethane copolymers sold under the trade name Pecogel GC-310 by the company UCIB or alternatively under the names Aquamere C 1031 and C 1511 by the company Blagden Chemicals,
the quaternized or non-quaternized PVP/dimethylaminoethyl methacrylate/C8 to C16 olefin copolymers sold under the names Ganex ACP 1050 to 1057, 1062 to 1069 and 1079 to 1086 by the company ISP,
the PVP/dimethylaminoethyl methacrylate/vinylcaprolactam copolymer sold under the name Gaffix VC 713 by the company ISP.

b) vinylpyrrolidone polymers containing methacrylamidopropyltrimethylammonium (MAPTAC) units, for example:
the vinylpyrrolidone/MAPTAC copolymers sold under the trade names Gafquat ACP 1011 and Gafquat HS 100 by the company ISP, c) vinylpyrrolidone polymers containing methylvinylimidazolium units, for example:
the PVP/methylvinylimidazolium chloride copolymers sold under the names Luviquat FC 370, FC 550, FC 905 and HM 552 by the company BASF,
the PVP/methylvinylimidazolium chloride/vinylimidazole copolymer sold under the name Luviquat 8155 by the company BASF,
the PVP/methylvinylimidazolium methosulphate copolymer sold under the name Luviquat MS 370 by the company BASF.

The concentration of substantive polymer (ii) in the dye composition according to the invention can range from about 0.01 to about 10% relative to the total weight of the dye composition, and preferably from 0.1 to 5%.

The medium suitable for dyeing (or support) generally comprises water or a mixture of water and at least one organic solvent, which can dissolve the compounds that would not be sufficiently soluble in the water. Preferred organic solvents include, for example, $C_1$-$C_4$ lower alkanols, such as ethanol and isopropanol;

aromatic alcohols such as benzyl alcohol or phenoxyethanol, as well as similar products and mixtures thereof.

The solvents can be present in preferred proportions ranging from about 1 to about 40% by weight relative to the total weight of the dye composition, and even more preferably from about 5 to about 30% by weight.

The pH of the dye composition in accordance with the invention generally ranges from about 2 to about 11 and preferably from about 5 to about 10. The pH can be adjusted to the desired value using acidifying or basifying agents typically used in the dyeing of keratin fibers.

Examples of acidifying agents include inorganic or organic acids, such as hydrochloric acid, orthophosphoric acid, sulphuric acid, carboxylic acids, such as acetic acid, tartaric acid, citric acid or lactic acid, and sulphonic-acids.

Examples of basifying agents include aqueous ammonia, alkaline carbonates, alkanolamines, such as mono-, di- and triethanolamine and derivatives thereof, sodium hydroxide, potassium hydroxide and the compounds of formula (VII) below:

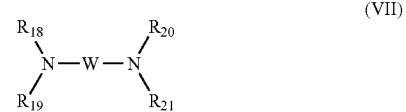

wherein W is a propylene residue optionally substituted with a hydroxyl group or a $C_1$-$C_6$ alkyl radical; $R_{18}$, $R_{19}$, $R_{20}$ and $R_{21}$ are identical or different and represent a hydrogen atom or a $C_1$-$C_6$ alkyl or $C_1$-$C_6$ hydroxyalkyl radical.

In addition to the at least one cationic direct dye (i) defined above, the dye composition in accordance with the invention can contain at least one additional direct dye that can be selected, for example, from nitrobenzene dyes, anthraquinone dyes, naphthoquinone dyes, triarylmethane dyes, xanthine dyes and azo dyes which are non-cationic.

When it is intended for oxidation dyeing, the dye composition in accordance with the invention contains, in addition to the at least one cationic direct dye (i), at least one oxidation base selected from the oxidation bases conventionally used for oxidation dyeing, for example, para-phenylenediamines, bis(phenyl)alkylenediamines, para-aminophenols, ortho-aminophenols and heterocyclic bases.

When they are used, the at least one oxidation base is preferably present in an amount ranging from about 0.0005 to about 12% by weight relative to the total weight of the dye composition, and even more preferably from about 0.005 to about 6% by weight relative to the total weight of the dye composition.

When it is intended for oxidation dyeing, the dye composition in accordance with the invention can also contain, in addition to the at least one cationic direct dye (i), the at least one substantive polymer (ii), and the at least one oxidation base, at least one coupler so as to modify the shades obtained or to enrich them with glints, by using the at least one cationic direct dye (i) and the at least one oxidation base.

The at least one coupler that can be used in the dye composition in accordance with the invention can be selected from the couplers conventionally used in oxidation dyeing, for example, meta-phenylenediamines, meta-aminophenols, meta-diphenols and heterocyclic couplers.

When they are present, the at least one coupler is preferably present in an amount ranging from about 0.0001 to about 10% by weight relative to the total weight of the dye composition, and even more preferably from about 0.005 to about 5% by weight relative to the total weight of the dye composition.

The dye composition in accordance with the invention can also contain various adjuvants conventionally used in compositions for dyeing the hair, such as antioxidants, penetrating agents, sequestering agents, fragrances, buffers, dispersing agents, surfactants, film-forming agents, ceramides, preserving agents, screening agents and opacifiers.

Needless to say, a person skilled in the art will take care to select this or these optionally complementary compounds such that the advantageous properties intrinsically associated with the dye composition in accordance with the invention are not, or are not substantially, adversely affected by the addition(s) envisaged.

The dye composition according to the invention can be in various forms, such as in the form of liquids, shampoos, creams or gels or in any other form which is suitable for dyeing keratin fibers, and, especially, human hair. The presentation in shampoo form is particularly preferred.

When the combination of the at least one cationic direct dye (i) and of the at least one substantive polymer (ii) according to the invention is used in a composition intended for oxidation dyeing (at least one oxidation base is then used, optionally in the presence of at least one coupler), or when it is used in a composition intended for lightening direct dyeing, then the dye composition in accordance with the invention also contains at least one oxidizing agent selected, for example, from hydrogen peroxide, urea peroxide, alkali metal bromates, persalts, such as perborates and persulphates, and enzymes, such as peroxidases, lactases and two-electron oxidoreductases. The use of hydrogen peroxide or of enzymes is particularly preferred.

Another subject of the invention is a method for dyeing keratin fibers, especially human keratin fibers, such as the hair, using the dye composition as defined above.

According to a first variant of this dyeing process in accordance with the invention, at least one dye composition as defined above is applied to the keratin fibers, for a period of time sufficient to develop the desired coloration, after which the fibers are rinsed, optionally washed with shampoo, rinsed again and dried.

The time required to develop the coloration on the keratin fibers generally ranges from 3 to 60 minutes, and more preferably ranges from 5 to 40 minutes.

According to a second variant of this dyeing process in accordance with the invention, at least one dye composition as defined above is applied to the keratin fibers, for a period which is sufficient to develop the desired coloration, without final rinsing.

According to a specific embodiment of this dyeing process, when the dye composition in accordance with the invention contains at least one oxidation base and at least one oxidizing agent, the dyeing process includes a first step which comprises separately storing, on the one hand, a composition (A1) comprising, in a medium suitable for dyeing, at least one cationic direct dye (i) as defined above and at least one oxidation base, and, on the other hand, a composition (B1) containing, in a medium suitable for dyeing, at least one oxidizing agent, followed by mixing them together at the time of use, before applying this mixture to the keratin fibers, the composition (A1) or the composition (B1) containing the cationic or amphoteric substantive polymer (ii) as defined above.

According to another specific embodiment of this dyeing process, and when the dye composition in accordance with the invention contains at least one oxidizing agent, the dyeing process includes a first step which comprises separately storing, on the one hand, a composition (A2) comprising, in a medium suitable for dyeing, at least one cationic direct dye (i) as defined above, and, on the other hand, a composition (B2) containing, in a medium suitable for dyeing, at least one oxidizing agent, followed by mixing them together at the time of use, before applying this mixture to the keratin fibers, the composition (A2) or the composition (B2) containing the cationic or amphoteric substantive polymer as defined above.

Another subject of the invention is a multi-compartment dyeing device or "kit" or any other multi-compartment packaging system, a first compartment of which contains composition (A1) or (A2) as defined above and a second compartment of which contains composition (B1) or (B2) as defined above. These devices can be equipped with a means for applying the desired mixture to the hair, such as the devices described in French Patent No. FR-2,586,913 in the name of L'Oréal.

The present invention is further illustrated by the following examples which are designed to teach those of ordinary skill in the art how to practice the invention. The following examples are intended to illustrate the invention without limiting its scope.

EXAMPLES

Example 1

The dye composition below was prepared:

| | |
|---|---|
| Cationic direct dye of formula I(2) | 0.125 g |
| para-Aminophenol | 0.120 g |
| 5-N-β-Hydroxyethylamino-2-methylphenol | 0.125 g |
| Substantive polymer: copolymer of diallyldimethyl-ammonium chloride and of acrylic acid (80/20 by weight), sold under the name Merquat 280 by the company Calgon | 1.0 g A.M.* |
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M.* |

-continued

| | |
|---|---|
| Oleic acid | 3.0 g |
| Oleylamine containing 2 mol of ethylene oxide, sold under the trade name Ethomeen O12 by the company Akzo | 7.0 g |
| Diethylaminopropyl laurylaminosuccinamate, sodium salt, containing 55% A.M. | 3.0 g A.M.* |
| Oleyl alcohol | 5.0 g |
| Oleic acid diethanolamide | 12.0 g |
| Propylene glycol | 3.5 g |
| Dipropylene glycol | 0.5 g |
| Propylene glycol monomethyl ether | 9.0 g |
| Ethanol | 7.0 g |
| Sodium metabisulphite as an aqueous solution containing 35% A.M. | 0.455 g A.M.* |
| Ammonium acetate | 0.8 g |
| Antioxidant, sequestering agent | qs |
| Fragrance, preserving agent | qs |
| Aqueous ammonia containing 20% $NH_3$ | 10.0 g |

A.M.*: Active material

At the time of use, this composition was mixed with an equal amount of an aqueous 20-volume hydrogen peroxide solution (6% by weight).

The resulting mixture was applied for 30 minutes to locks of natural grey hair containing 90% white hairs. The locks of hair were then rinsed, washed with standard shampoo, and then dried.

The locks of hair were dyed a light blonde shade with an intense red glint.

Example 2

The dye composition below was prepared:

| | |
|---|---|
| Cationic direct dye of formula I(14) | 0.09 g |
| Substantive polymer of polyquaternary ammonium type of formula (IV) | 1.0 g A.M.* |
| Nonylphenol containing 9 mol of ethylene oxide | 8.0 g |
| 2-Amino-2-methylpropanol | qs pH 9 |
| Demineralized water | qsp 100 g |

A.M.*: Active material

The above composition was applied for 30 minutes to locks of natural grey hair containing 90% white hairs. The locks of hair were then rinsed, washed with a standard shampoo and then dried.

The locks of hair were dyed an intense coppery shade.

The foregoing written description relates to various embodiments of the present invention. Numerous changes and modifications may be made therein without departing from the spirit and scope of the invention as defined in the following claims.

What is claimed is:

1. A composition for dyeing keratin fibers, said composition comprising, in a medium suitable for dyeing,
(i) at least one cationic direct dye of formula (I), or (III) below:
wherein, in said formula (I):

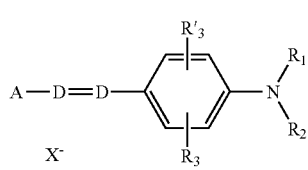

(I)

D represents a nitrogen atom or a —CH group, $R_1$ and $R_2$ are identical or different and represent a hydrogen atom, a $C_1$-$C_4$ alkyl radical which is unsubstituted or substituted with a —CN, —OH or —$NH_2$, or $R_1$ and $R_2$ form, with a carbon atom of the benzene ring, a heterocycle containing at least one heteroatom chosen from oxygen and nitrogen and which is unsubstituted or substituted with one or more $C_1$-$C_4$ alkyl radicals or a 4'-aminophenyl radical;

$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;

$X^-$ represents an anion;

A represents a group selected from structures below:

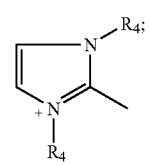

$A_1$

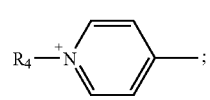

$A_4$

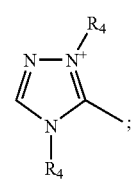

$A_6$

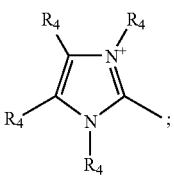

$A_7$

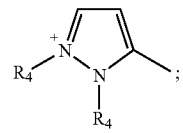

$A_8$

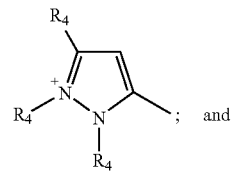

$A_9$ ; and

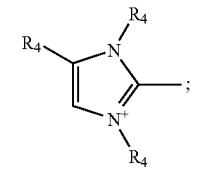

$A_{19}$ wherein
$R_4$ represents a $C_1$-$C_4$ alkyl radical which is unsubstituted or substituted with a hydroxyl radical; and with the provisos that when D represents —CH, A represents $A_4$ or $A_{13}$, and $R_3$ is other than an alkoxy radical, then $R_1$ and $R_2$ do not simultaneously represent a hydrogen atom; and when D represents N, A is chosen from $A_1$, $A_6$-$A_9$ and $A_{19}$;

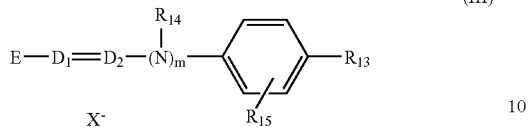
(III)

wherein, in said formulae (III):

$R_{13}$ represents a hydrogen atom, a $C_1$-$C_4$ alkoxy radical, a halogen atom, and an amino radical;

$R_{14}$ represents a hydrogen atom, a $C_1$-$C_4$ alkyl radical, or $R_{14}$ forms, with a carbon atom of the benzene ring, a heterocycle which is optionally oxygenated and/or substituted with at least one $C_1$-$C_4$ alkyl group;

$R_{15}$ represents a hydrogen atom or a halogen atom;

$D_1$ and $D_2$, which are identical or different, are chosen from a nitrogen atom and a —CH group;

m=0 or 1;

with the proviso that when $R_{13}$ represents an unsubstituted amino group, then $D_1$ and $D_2$ simultaneously represent a —CH group and m=0;

$X^-$ represents an anion; and

E represents a group from structures below:

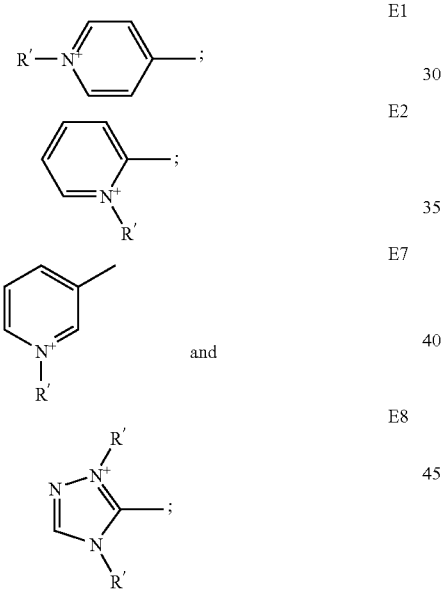

wherein R' represents a $C_1$-$C_4$ alkyl radical;

with the proviso that when m=0 and $D_1$ represents a nitrogen atom, then E can also represents a group of structure E9 below:

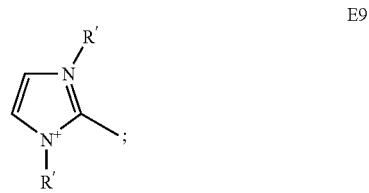

wherein R' represents a $C_1$-$C_4$ alkyl radical; with the further proviso that in said formula (III) when $D_1$ and $D_2$ are simultaneously a nitrogen atom, m=0, $R_{13}$ is an amino radical and $R_{15}$ is a hydrogen atom, then E is chosen from $E_3$ to $E_5$, $E_7$ and $E_8$; and (ii) at least one cationic or amphoteric substantive polymer chosen from:
(a) cellulosic cationic derivatives with the exception of polymeric quaternary ammonium salts of hydroxyethyl cellulose reacted with a trimethyl ammonium substituted epoxide;
(b) copolymers of dimethyldiallylammonium halide and of (meth)acrylic acid;
(c) methacryloyloxyethyltrimethylammonium halide homopolymers and copolymers;
(d) polyquaternary ammonium polymers selected from:
polymers of repeating units having formula (IV) below:

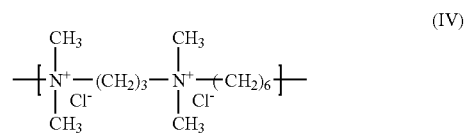

polymers of repeating units having formula (V) below:

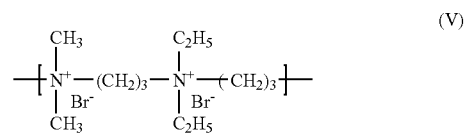

and polymers of repeating units having formula (VI) below:

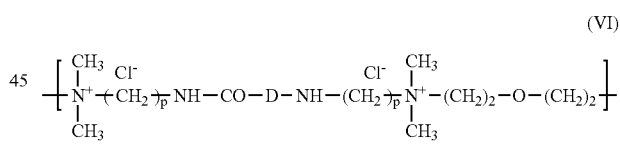

wherein p represents an integer ranging from 1 to 6 approximately, D is zero or represents a group —$(CH_2)_r$—CO— wherein r represents a number equal to 4 or 7; and
(e) vinylpyrrolidone copolymers containing cationic units.

2. A composition according to claim 1, wherein in said formula (I), or (III), $X^-$ represents an anion of chloride, methyl sulfate, or acetate.

3. A composition according to claim 1, wherein said keratin fibers are human keratin fibers.

4. A composition according to claim 3, wherein said human keratin fibers are human hair.

5. A composition according to claim 1, wherein said at least one cationic direct dye of formula (I) is selected from the compounds having structures below:

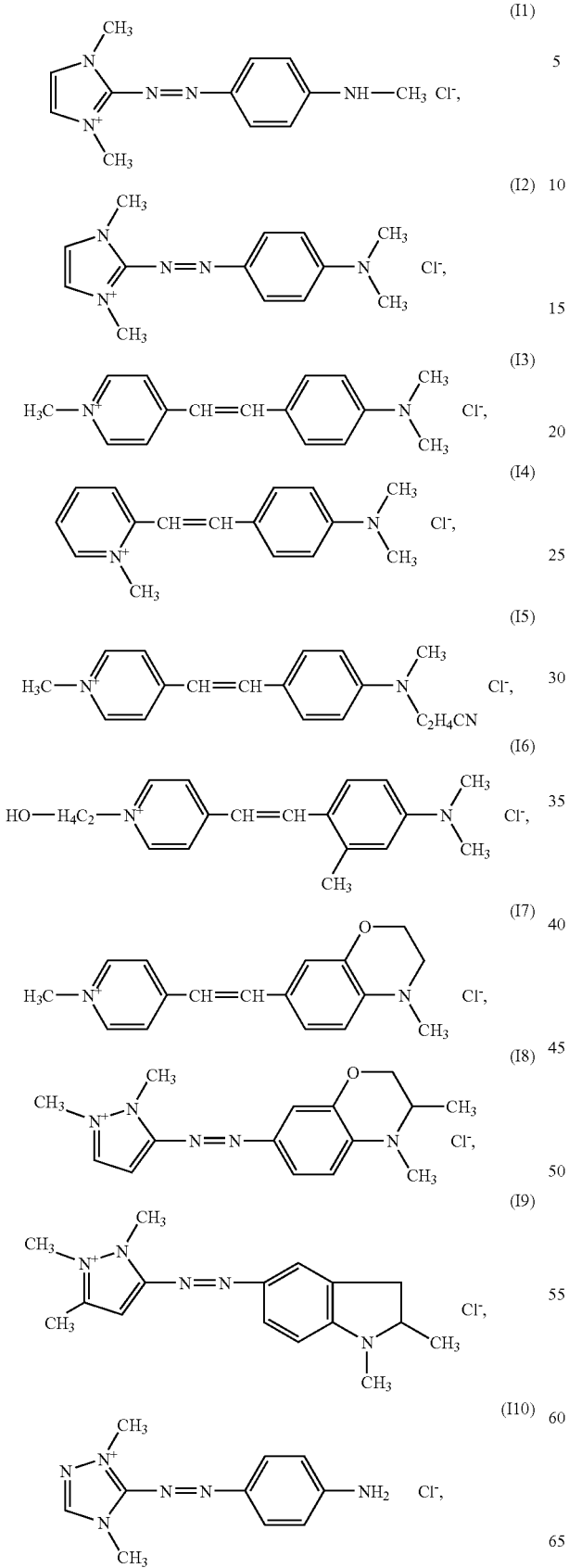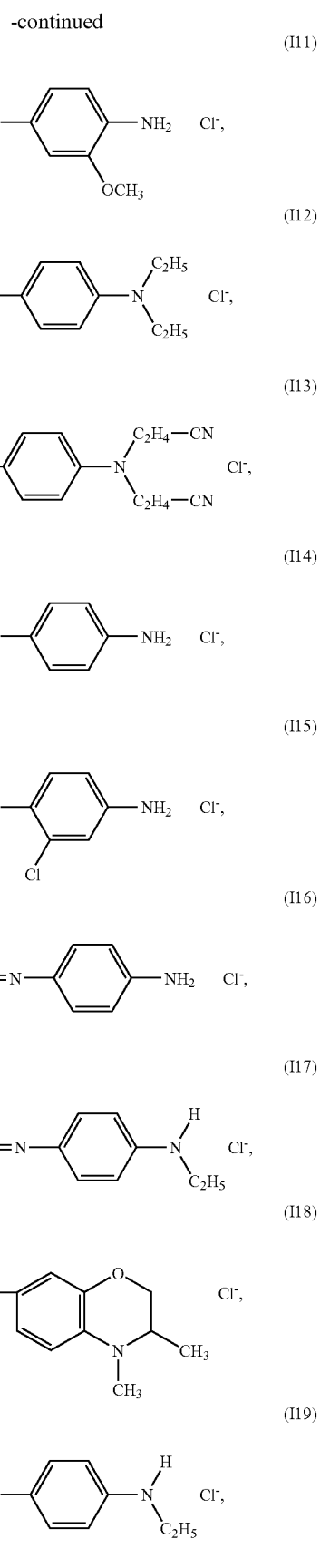

-continued (I20)

(I21)

(I22)

(I23)

(I24)

(I25)

(I28)

(I29)

(I31)

-continued (I43)

(I51)

6. A composition according to claim 5, wherein said at least one cationic direct dye has structure (I1), (I2), (I14) or (I31).

7. A composition according to claim 1, wherein said at least one cationic direct dye of formula (III) is selected from the compounds having structures below:

(III4)

(III5)

(III6)

(III7)

(III8)

(III9)

(III10)

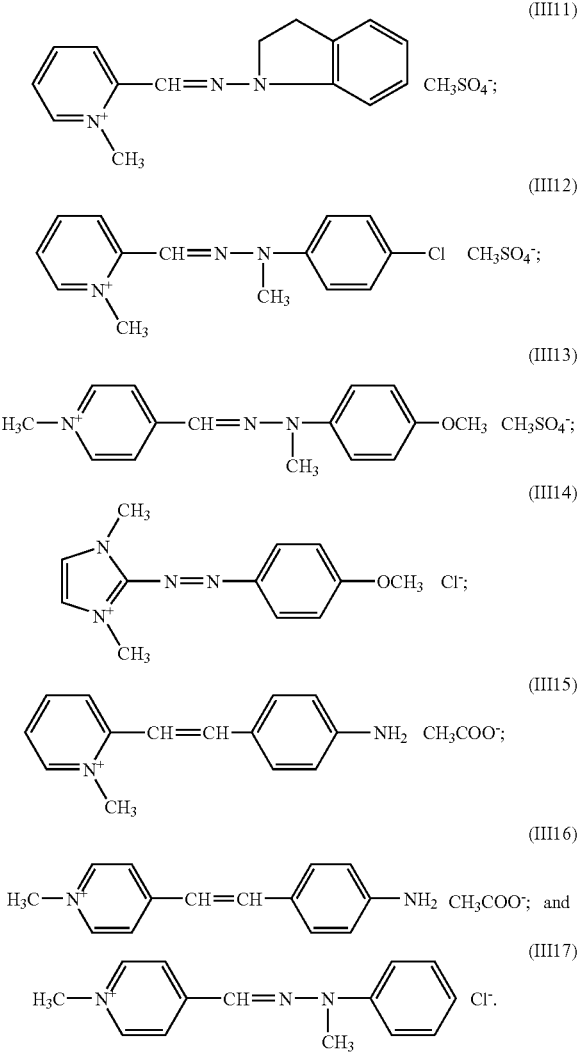

8. A composition according to claim 7, wherein said at least one cationic direct dye of formula (III) has structure (III4), (III5) or (III13).

9. A composition according to claim 1, wherein said at least one cationic direct dye present in an amount ranging from about 0.001 to about 10% by weight relative to the total weight of the composition.

10. A composition according to claim 9, wherein said at least one cationic direct dye present in amount ranging from about 0.005 to about 5% by weight relative to the total weight of the composition.

11. A composition according to claim 1, wherein said at least one cationic or amphoteric substantive polymer is a polymeric quaternary ammonium salt of hydroxyethyl cellulose reacted with a lauryl dimethyl ammonium substituted epoxide.

12. A composition according to claim 1, wherein said at least one cationic or amphoteric substantive polymer is a copolymer of dimethyldiallylammonium chloride and of acrylic acid (80/20 by weight).

13. A composition according to claim 1, wherein said at least one cationic or amphoteric substantive polymer is a crosslinked poly(methacryloyloxyethyltrimethylammonium chloride) homopolymer, as a 50% dispersion in mineral oil; the crosslinked copolymer of acrylamide and of methacryloyloxyethyltrimethylammonium chloride (20/80 by weight), as a 50% dispersion in mineral oil; or the methosulphate of the copolymer of methacryloyloxyethyl-trimethylammonium and of methacryloyloxyethyldimethyl-acetylammonium.

14. A composition according to claim 1, wherein said at least one cationic or amphoteric substantive polymer is:
 a) a vinylpyrrolidone polymer containing dimethylaminoethyl methacrylate units;
 b) a vinylpyrrolidone polymer containing methacrylamidopropyltrimethylammonium units; or
 c) a vinylpyrrolidone polymer containing methylvinylimidazolium units.

15. A composition according to claim 1, wherein said at least one cationic or amphoteric substantive polymer is present in an amount ranging from about 0.01 to about 10% by weight relative to the total weight of the composition.

16. A composition according to claim 15, wherein said at least one cationic or amphoteric substantive polymer is present in an amount ranging from about 0.1 to about 5% by weight relative to the total weight of the composition.

17. A composition according to claim 1, wherein said medium suitable for dyeing comprises water or a mixture of water and at least one organic solvent.

18. A composition according to claim 1, wherein said composition has a pH ranging from about 2 to about 11.

19. A composition according to claim 18, wherein said composition has a pH ranging from about 5 to about 10.

20. A composition according to claim 1, further comprising at least one additional direct dye.

21. A composition according to claim 20, wherein said at least one additional direct dye is a nitrobenzene dye, anthraquinone dye, naphthoquinone dye, triarylmethane dye, xanthine dye, or an azo dye that is non-cationic.

22. A composition according to claim 1, further comprising at least one oxidation base selected from para-phenylenediamines, bis(phenyl)alkylenediamines, para-aminophenols, ortho-aminophenols and heterocyclic bases.

23. A composition according to claim 22, wherein said at least one oxidation base is present in an amount ranging from about 0.0005 to about 12% by weight relative to the total weight of the dye composition.

24. A composition according to claim 23, wherein said at least one oxidation base is present in an amount ranging from about 0.005 to about 6% by weight relative to the total weight of the dye composition.

25. A composition according to claim 22, further comprising at least one coupler selected from meta-phenylenediamines, meta-aminophenols, meta-diphenols and heterocyclic couplers.

26. A composition according to claim 25, wherein said at least one coupler is present in an amount ranging from about 0.0001 to about 10% by weight relative to the total weight of the dye composition.

27. A composition according to claim 26, wherein said at least one coupler is present in an amount ranging from about 0.005 to about 5% by weight relative to the total weight of the dye composition.

28. A composition according to claim 1, further comprising at least one oxidizing agent.

29. A composition according to claim 28, wherein said at least one oxidizing agent is hydrogen peroxide, urea peroxide, alkali metal bromate, a persalt, or an enzyme.

30. A method for dyeing keratin fibers, said method comprising applying at least one dyeing composition comprising, in a medium suitable for dyeing, (i) at least one cationic direct dye of formula (I), or (III) below:

wherein, in said formula (I):

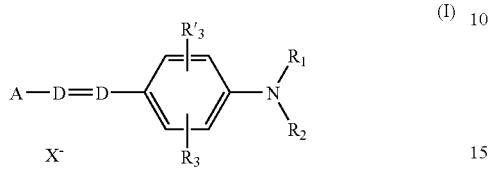
(I)

D represents a nitrogen atom or a —CH group, $R_1$ and $R_2$ are identical or different and represent a hydrogen atom, a $C_1$-$C_4$ alkyl radical which is unsubstituted or substituted with a —CN, —OH or —NH$_2$, or $R_1$ and $R_2$ form, with a carbon atom of the benzene ring, a heterocycle containing at least one heteroatom chosen from oxygen and nitrogen and which is unsubstituted or substituted with one or more $C_1$-$C_4$ alkyl radicals or a 4'-aminophenyl radical;

$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;

X— represents an anion;

A represents a group selected from structures below:

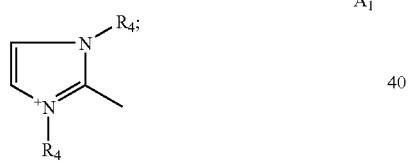
$A_1$

A represents a group selected from structures below:

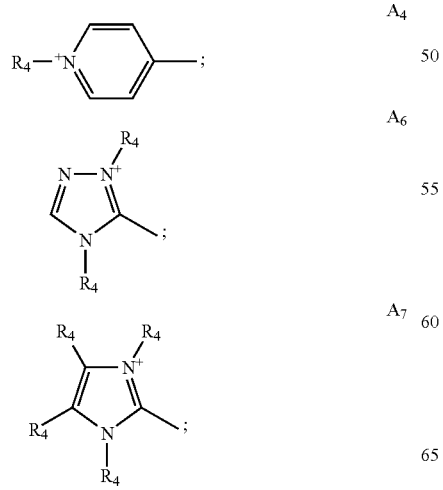
$A_4$
$A_6$
$A_7$

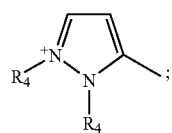
$A_8$

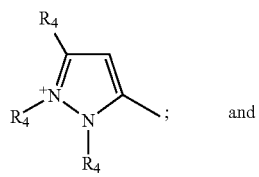
$A_9$ and

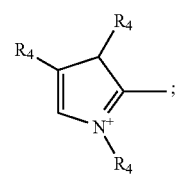
$A_{19}$ wherein $R_4$ represents a $C_1$-$C_4$ alkyl radical which is unsubstituted or substituted with a hydroxyl radical; and with the provisos that when D represents —CH, A represents $A_4$ or $A_{13}$, and $R_3$ is other than an alkoxy radical, then $R_1$ and $R_2$ do not simultaneously represent a hydrogen atom; and when D represents N, A is chosen from $A_1$, $A_6$-$A_9$ and $A_{19}$;

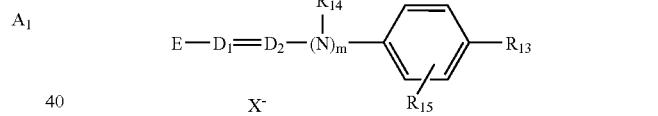
(III)

wherein, in said formulae (III):

$R_{13}$ represents a hydrogen atom, a $C_1$-$C_4$ alkoxy radical, a halogen atom, and an amino radical;

$R_{14}$ represents a hydrogen atom, a $C_1$-$C_4$ alkyl radical, or $R_{14}$ forms, with a carbon atom of the benzene ring, a heterocycle which is optionally oxygenated and/or substituted with at least one $C_1$-$C_4$ alkyl group;

$R_{15}$ represents a hydrogen atom or a halogen atom;

$D_1$ and $D_2$, which are identical or different, are chosen from a nitrogen atom and a —CH group;

m=0 or 1;

with the proviso that when $R_{13}$ represents an unsubstituted amino group, then $D_1$ and $D_2$ simultaneously represent a —CH group and m=0;

X⁻ represents an anion; and

E represents a group from structures below:

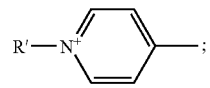
E1

-continued

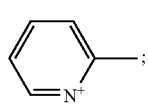
E2

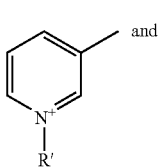
E7 and

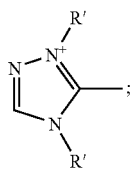
E8 wherein R' represents a $C_1$-$C_4$ alkyl radical;
with the proviso that when m=0 and $D_1$ represents a nitrogen atom, then E can also represents a group of structure E9 below:

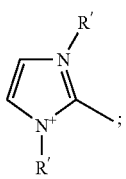
E9 wherein R' represents a $C_1$-$C_4$ alkyl radical; with the further proviso that in said formula (III) when $D_1$ and $D_2$ are simultaneously a nitrogen atom, m=0, $R_{13}$ is an amino radical and $R_{15}$ is a hydrogen atom, then E is chosen from $E_3$ to $E_5$, $E_7$ and $E_8$; and (ii) at least one cationic or amphoteric substantive polymer chosen from:
(a) cellulosic cationic derivatives with the exception of polymeric quaternary ammonium salts of hydroxyethyl cellulose reacted with a trimethyl ammonium substituted epoxide;
(b) copolymers of dimethyldiallylammonium halide and of (meth)acrylic acid;
(c) methacryloyloxyethyltrimethylammonium halide homopolymers and copolymers;
(d) polyquaternary ammonium polymers selected from:
polymers of repeating units having formula (IV) below:

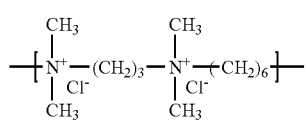
(IV)

polymers of repeating units having formula (V) below:

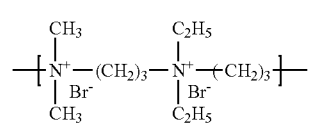
(V)

and polymers of repeating units having formula (VI) below:

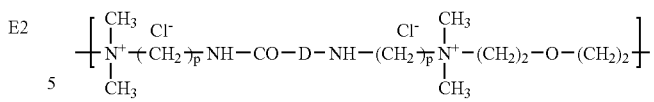
(VI)

wherein p represents an integer ranging from 1 to 6 approximately, D is zero or represents a group —$(CH_2)_r$—CO— wherein r represents a number equal to 4 or 7; and (e) vinylpyrrolidone copolymers containing cationic units to said keratin fibers, and allowing said at least one dyeing composition to remain on said keratin fibers for a period of time sufficient to develop the desired coloration.

31. A method for dyeing keratin fibers according to claim 30, further comprising rinsing said keratin fibers after said period of time sufficient to develop the desired coloration.

32. A method for dyeing keratin fibers according to claim 31, further comprising, after said rinsing, washing said keratin fibers with shampoo, rinsing said keratin fibers again, and drying said keratin fibers.

33. The method according to claim 31, wherein said period of time ranges from 3 to 60 minutes.

34. The method according to claim 33, wherein said period of time ranges from 5 to 40 minutes.

35. A method for dyeing keratin fibers, said method comprising
(1) mixing a composition (A1), said composition (A1) comprising at least one cationic direct dye of formula (I), or (III) below: wherein, in said formula (I):

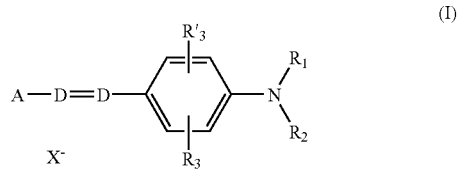
(I)

D represents a nitrogen atom or a —CH group,
$R_1$ and $R_2$ are identical or different and represent a hydrogen atom, a $C_1$-$C_4$ alkyl radical which is unsubstituted or substituted with a —CN, —OH or —$NH_2$, or $R_1$ and $R_2$ form, with a carbon atom of the benzene ring, a heterocycle containing at least one heteroatom chosen from oxygen and nitrogen and which is unsubstituted or substituted with one or more $C_1$-$C_4$ alkyl radicals or a 4'-aminophenyl radical;
$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;
$X^-$ represents an anion;
A represents a group selected from structures below:

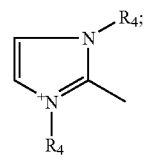
$A_1$

A represents a group selected from structures below:

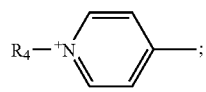
A4

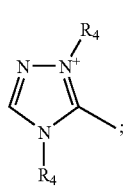
A6

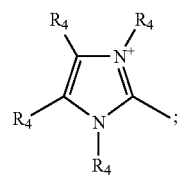
A7

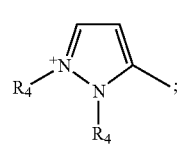
A8

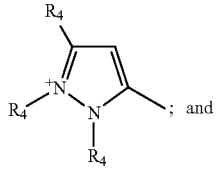
A9

; and

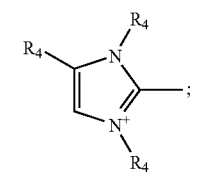
A19 wherein
  $R_4$ represents a $C_1$-$C_4$ alkyl radical which is unsubstituted or substituted with a hydroxyl radical; and
with the provisos that when D represents —CH, A represents $A_4$ or $A_{13}$, and $R_3$ is other than an alkoxy radical, then $R_1$ and $R_2$ do not simultaneously represent a hydrogen atom; and
when D represents N, A is chosen from $A_1$, $A_6$-$A_9$ and $A_{19}$;

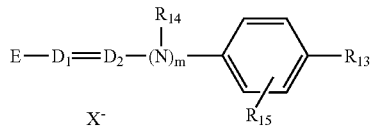
(III)

wherein, in said formulae (III):
$R_{13}$ represents a hydrogen atom, a $C_1$-$C_4$ alkoxy radical, a halogen atom, and an amino radical;
$R_{14}$ represents a hydrogen atom, a $C_1$-$C_4$ alkyl radical, or $R_{14}$ forms, with a carbon atom of the benzene ring, a heterocycle which is optionally oxygenated and/or substituted with at least one $C_1$-$C_4$ alkyl group;
$R_{15}$ represents a hydrogen atom or a halogen atom;

$D_1$ and $D_2$, which are identical or different, are chosen from a nitrogen atom and a —CH group;
m=0 or 1;
with the proviso that when $R_{13}$ represents an unsubstituted amino group, then $D_1$ and $D_2$ simultaneously represents a —CH group and m=0;
$X^-$ represents an anion; and
E represents a group from structures below:

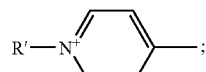
E1

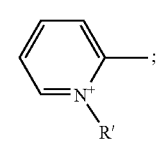
E2

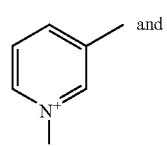
E7 and

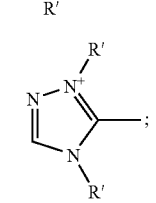
E8 wherein R' represents a $C_1$-$C_4$ alkyl radical;
with the proviso that when m=0 and $D_1$ represents a nitrogen atom, then E can also represents a group of structure E9 below:

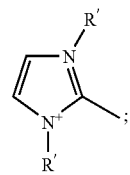
E9 wherein R' represents a $C_1$-$C_4$ alkyl radical; with the further proviso that in said formula (III) when $D_1$ and $D_2$ are simultaneously a nitrogen atom, m=0, $R_{13}$ is an amino radical and $R_{15}$ is a hydrogen atom, then E is chosen from $E_3$ to $E_5$, $E_7$ and $E_8$,
and at least one oxidation base with a composition (B1), said composition (B1) comprising, in a medium suitable for dyeing, at least one oxidizing agent, wherein said composition (A1) or said composition (B1) contains at least one cationic or amphoteric substantive polymer chosen from:
(a) cellulosic cationic derivatives with the exception of polymeric quaternary ammonium salts of hydroxyethyl cellulose reacted with a trimethyl ammonium substituted epoxide;
(b) copolymers of dimethyldiallylammonium halide and of (meth)acrylic acid;
(c) methacryloyloxyethyltrimethylammonium halide homopolymers and copolymers;

(d) polyquaternary ammonium polymers selected from: polymers of repeating units having formula (IV) below:

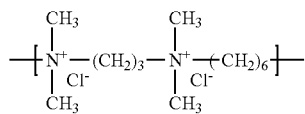
(IV)

polymers of repeating units having formula (V) below:

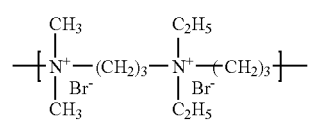
(V)

and polymers of repeating units having formula (VI) below:

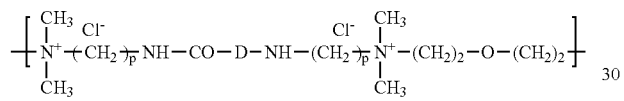
(VI)

wherein p represents an integer ranging from 1 to 6 approximately, D is zero or represents a group —$(CH_2)_r$—CO— wherein r represents a number equal to 4 or 7; and (e) vinylpyrrolidone copolymers containing cationic units and (2) applying said mixture of said composition (A1) and said composition (B1) to said keratin fibers for a period of time sufficient to dye said keratin fibers, wherein said mixing occurs before the time of application to said keratin fibers.

36. A method for dyeing keratin fibers, said method comprising (1) mixing a composition (A2), said composition (A2) comprising at least one cationic direct dye of formula (I), or (III) below: wherein, in said formula (I):

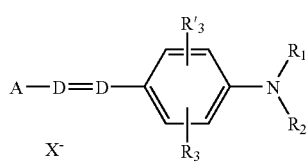
(I)

D represents a nitrogen atom or a —CH group, $R_1$ and $R_2$ are identical or different and represent a hydrogen atom, a $C_1$-$C_4$ alkyl radical which is unsubstituted or substituted with a —CN, —OH or —$NH_2$, or $R_1$ and $R_2$ form, with a carbon atom of the benzene ring, a heterocycle containing at least one heteroatom chosen from oxygen and nitrogen and which is unsubstituted or substituted with one or more $C_1$-$C_4$ alkyl radicals or a 4'-aminophenyl radical;

$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;

$X^-$ represents an anion;

A represents a group selected from structures below:

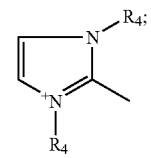
$A_1$

A represents a group selected from structures below:

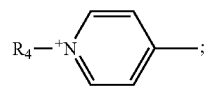
$A_4$

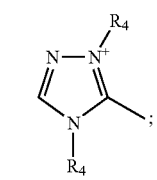
$A_6$

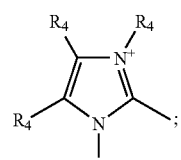
$A_7$

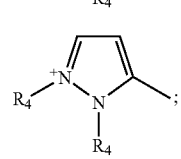
$A_8$

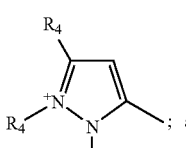
$A_9$; and

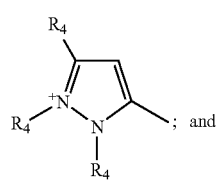
$A_{19}$ wherein $R_4$ represents a $C_1$-$C_4$ alkyl radical which is unsubstituted or substituted with a hydroxyl radical; and with the provisos that when D represents —CH, A represents $A_4$ or $A_{13}$, and $R_3$ is other than an alkoxy radical, then $R_1$ and $R_2$ do not simultaneously represent a hydrogen atom; and when D represents N, A is chosen from $A_1$, $A_6$-$A_9$ and $A_{19}$;

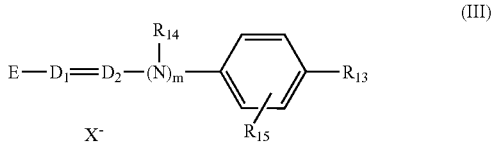

wherein, in said formulae (III):
R$_{13}$ represents a hydrogen atom, a C$_1$-C$_4$ alkoxy radical, a halogen atom, and an amino radical;
R$_{14}$ represents a hydrogen atom, a C$_1$-C$_4$ alkyl radical, or R$_{14}$ forms, with a carbon atom of the benzene ring, a heterocycle which is optionally oxygenated and/or substituted with at least one C$_1$-C$_4$ alkyl group;
R$_{15}$ represents a hydrogen atom or a halogen atom;
D$_1$ and D$_2$, which are identical or different, are chosen from a nitrogen atom and a —CH group;
m=0 or 1;
with the proviso that when R$_{13}$ represents an unsubstituted amino group, then D$_1$ and D$_2$ simultaneously represents a —CH group and m=0;
X$^-$ represents an anion; and
E represents a group from structures below:

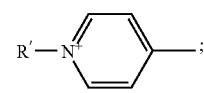
E1

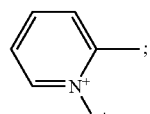
E2

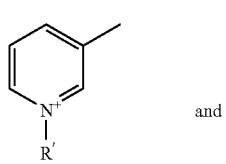
E7 and

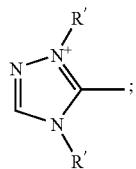
E8 wherein R' represents a C$_1$-C$_4$ alkyl radical:
with the proviso that when m=0 and D$_1$ represents a nitrogen atom, then E can also represents a group of structure E9 below:

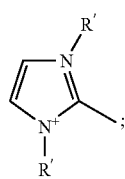
E9 wherein R' represents a C$_1$-C$_4$ alkyl radical; with the further proviso that in said formula (III) when D$_1$ and D$_2$ are simultaneously a nitrogen atom, m=0, R$_{13}$ is an amino radical and R$_{15}$ is a hydrogen atom, then E is chosen from E$_3$ to E$_5$, E$_7$ and E$_8$, with a composition (B2), said composition (B2) comprising, in a medium suitable for dyeing, at least one oxidizing agent, wherein said composition (A2) or said composition (B2) contains at least one cationic or amphoteric substantive polymer chosen from:

(a) cellulosic cationic derivatives with the exception of polymeric quaternary ammonium salts of hydroxyethyl cellulose reacted with a trimethyl ammonium substituted epoxide;

(b) copolymers of dimethyldiallylammonium halide and of (meth)acrylic acid;

(c) methacryloyloxyethyltrimethylammonium halide homopolymers and copolymers;

(d) polyquaternary ammonium polymers selected from:
polymers of repeating units having formula (IV) below:

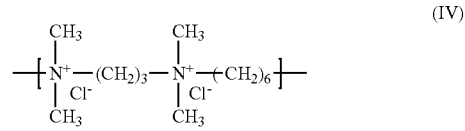

polymers of repeating units having formula (V) below:

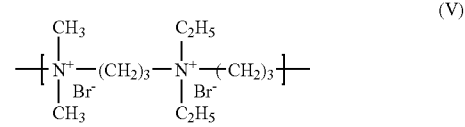

and polymers of repeating units having formula (VI) below:

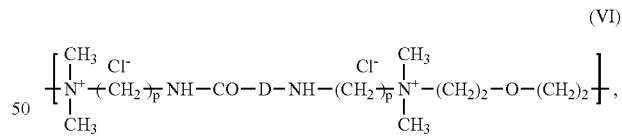

wherein p represents an integer ranging from 1 to 6 approximately, D is zero or represents a group —(CH$_2$)$_r$—CO— wherein r represents a number equal to 4 or 7; and (e) vinylpyrrolidone copolymers containing cationic units and (2) applying said mixture of said composition (A2) and said composition (B2) to said keratin fibers for a period of time sufficient to dye said keratin fibers, wherein said mixing occurs before the time of application to said keratin fibers.

37. A multi-component dyeing device or multi-compartment dyeing kit for dyeing keratin fibers comprising at least two compartments, wherein a first compartment comprises a composition (A1), said composition (A1) comprising at least one cationic direct dye of formula (I), or (III) below: wherein, in said formula (I):

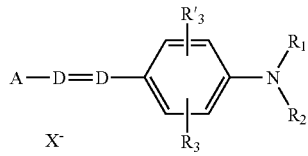

(I)

D represents a nitrogen atom or a —CH group, $R_1$ and $R_2$ are identical or different and represent a hydrogen atom, a $C_1$-$C_4$ alkyl radical which is unsubstituted or substituted with a —CN, —OH or —NH$_2$, or $R_1$ and $R_2$ form, with a carbon atom of the benzene ring, a heterocycle containing at least one heteroatom chosen from oxygen and nitrogen and which is unsubstituted or substituted with one or more $C_1$-$C_4$ alkyl radicals or a 4'-aminophenyl radical;

$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;

$X^-$ represents an anion;

A represents a group selected from structures below:

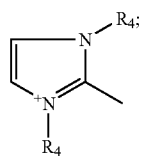

$A_1$

A represents a group selected from structures below:

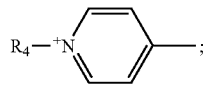

$A_4$

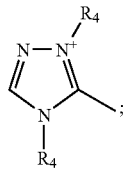

$A_6$

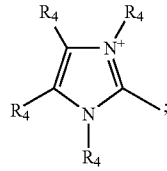

$A_7$

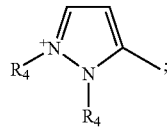

$A_8$

-continued

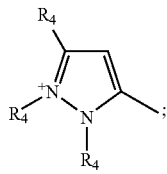

$A_9$

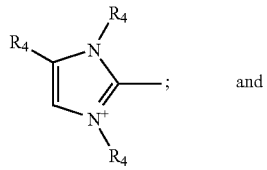

$A_{19}$ and wherein $R_4$ represents a $C_1$-$C_4$ alkyl radical which is unsubstituted or substituted with a hydroxyl radical; and with the provisos that when D represents —CH, A represents $A_4$ or $A_{13}$, and $R_3$ is other than an alkoxy radical, then $R_1$ and $R_2$ do not simultaneously represent a hydrogen atom; and when D represents N, A is chosen from $A_1$, $A_6$-$A_9$ and $A_{19}$;

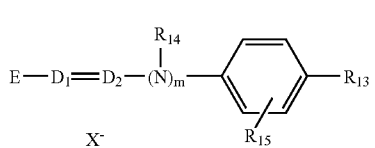

(III)

wherein, in said formulae (III):

$R_{13}$ represents a hydrogen atom, a $C_1$-$C_4$ alkoxy radical, a halogen atom, and an amino radical;

$R_{14}$ represents a hydrogen atom, a $C_1$-$C_4$ alkyl radical, or $R_{14}$ forms, with a carbon atom of the benzene ring, a heterocycle which is optionally oxygenated and/or substituted with at least one $C_1$-$C_4$ alkyl group;

$R_{15}$ represents a hydrogen atom or a halogen atom;

$D_1$ and $D_2$, which are identical or different, are chosen from a nitrogen atom and a —CH group;

m=0 or 1;

with the proviso that when $R_{13}$ represents an unsubstituted amino group, then $D_1$ and $D_2$ simultaneously represents a —CH group and m=0;

$X^-$ represents an anion; and

E represents a group from structures below:

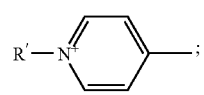

E1

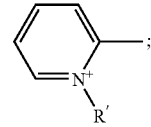

E2

-continued

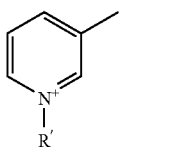
E7 and

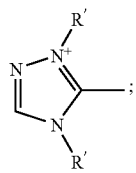
E8 wherein R' represents a $C_1$-$C_4$ alkyl radical;

with the proviso that when m=0 and $D_1$ represents a nitrogen atom, then E can also represents a group of structure E9 below:

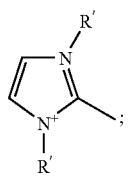
E9 wherein R' represents a $C_1$-$C_4$ alkyl radical; with the further proviso that in said formula (III) when $D_1$ and $D_2$ are simultaneously a nitrogen atom, m=0, $R_{13}$ is an amino radical and $R_{15}$ is a hydrogen atom, then E is chosen from $E_3$ to $E_5$, $E_7$ and $E_8$, and a second compartment comprises a composition (B1), said composition (B1) comprising, in a medium suitable for dyeing, at least one oxidizing agent, wherein said composition (A1) or said composition (B1) contains at least one cationic or amphoteric substantive polymer chosen from:

(a) cellulosic cationic derivatives with the exception of polymeric quaternary ammonium salts of hydroxyethyl cellulose reacted with a trimethyl ammonium substituted epoxide;

(b) copolymers of dimethyldiallylammonium halide and of (meth)acrylic acid;

(c) methacryloyloxyethyltrimethylammonium halide homopolymers and copolymers;

(d) polyquaternary ammonium polymers selected from:

polymers of repeating units having formula (IV) below:

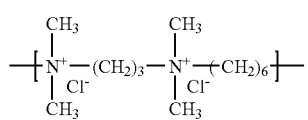
(IV)

polymers of repeating units having formula (V) below:

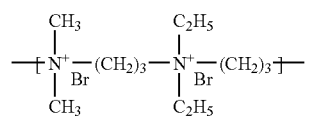
(V)

and polymers of repeating units having formula (VI) below:

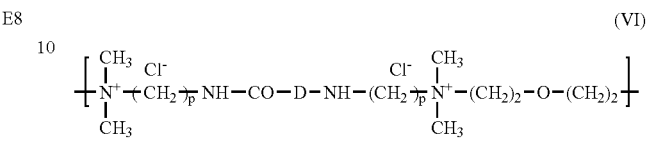
(VI)

wherein p represents an integer ranging from 1 to 6 approximately, D is zero or represents a group —$(CH_2)_r$—CO— wherein r represents a number equal to 4 or 7; and (e) vinylpyrrolidone copolymers containing cationic units.

38. A multi-component dyeing device or multi-compartment dyeing kit for dyeing keratin fibers comprising at least two compartments, wherein a first compartment comprises a composition (A2), said composition (A2) comprising at least one cationic direct dye of formula (I), or (III) below: wherein, in said formula (I):

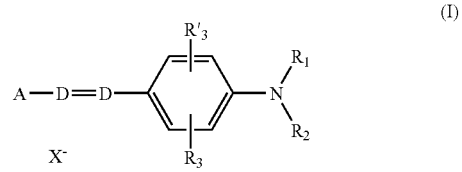
(I)

D represents a nitrogen atom or a —CH group, $R_1$ and $R_2$ are identical or different and represent a hydrogen atom, a $C_1$-$C_4$ alkyl radical which is unsubstituted or substituted with a —CN, —OH or —$NH_2$, or $R_1$ and $R_2$ form, with a carbon atom of the benzene ring, a heterocycle containing at least one heteroatom chosen from oxygen and nitrogen and which is unsubstituted or substituted with one or more $C_1$-$C_4$ alkyl radicals or a 4'aminophenyl radical;

$R_3$ and $R'_3$ are identical or different and represent a hydrogen atom, a halogen atom selected from chlorine, bromine, iodine and fluorine, a cyano group, a $C_1$-$C_4$ alkyl radical, or a $C_1$-$C_4$ alkoxy or acetyloxy radical;

$X^-$ represents an anion;

A represents a group selected from structures below:

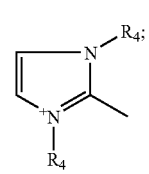
$A_1$

A represents a group selected from structures below:

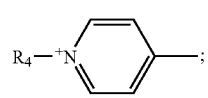
$A_4$

-continued

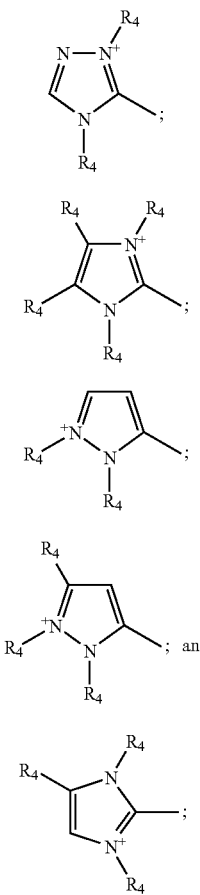

A6

A7

A8

A9

A19 wherein
R4 represents a C1-C4 alkyl radical which is unsubstituted or substituted with a hydroxyl radical; and
with the provisos that when D represents —CH, A represents A4 or A13, and R3 is other than an alkoxy radical, then R1 and R2 do not simultaneously represent a hydrogen atom; and
when D represents N, A is chosen from A1, A6-A9 and A19;

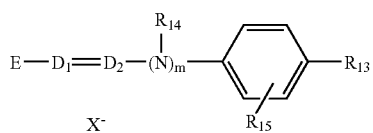

(III)

wherein, in said formulae (III):
R13, represents a hydrogen atom, a C1-C4 alkoxy radical, a halogen atom, and an amino radical;
R14 represents a hydrogen atom, a C1-C4 alkyl radical, or R14 forms, with a carbon atom of the benzene ring, a heterocycle which is optionally oxygenated and/or substituted with at least one C1-C4 alkyl group;
R15 represents a hydrogen atom or a halogen atom;
D1 and D2, which are identical or different, are chosen from a nitrogen atom and a —CH group;
m=0 or 1;

with the proviso that when R13 represents an unsubstituted amino group, then D1 and D2 simultaneously represents a —CH group and m=0;
X⁻ represents an anion; and
E represents a group from structures below:

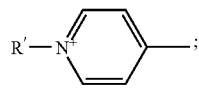

E1

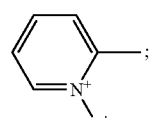

E2

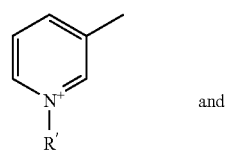

E7 and

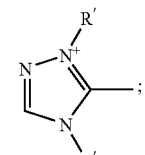

E8 wherein R' represents a C1-C4 alkyl radical;
with the proviso that when m=0 and D1 represents a nitrogen atom, then E can also represents a group of structure E9 below:

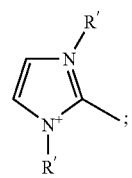

E9 wherein R' represents a C1-C4 alkyl radical: with the further proviso that in said formula (III) when D1 and D2 are simultaneously a nitrogen atom, m=0, R13 is an amino radical and R15 is a hydrogen atom, then E is chosen from E3 to E5, E7 and E8, and
a second compartment comprises a composition (B2), said composition (B2) comprising, in a medium suitable for dyeing, at least one oxidizing agent, wherein said composition (A2) or said composition (B2) contains at least one cationic or amphoteric substantive polymer chosen from:
(a) cellulosic cationic derivatives with the exception of polymeric quaternary ammonium salts of hydroxyethyl cellulose reacted with a trimethyl ammonium substituted epoxide;
(b) copolymers of dimethyldiallylammonium halide and of (meth)acrylic acid;
(c) methacryloyloxyethyltrimethylammonium halide homopolymers and copolymers;
(d) polyquaternary ammonium polymers selected from:

polymers of repeating units having formula (IV) below:

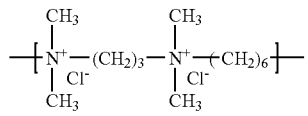
(IV)

polymers of repeating units having formula (V) below:

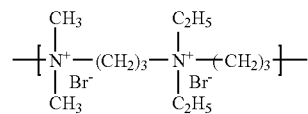
(V)

and polymers of repeating units having formula (VI) below:

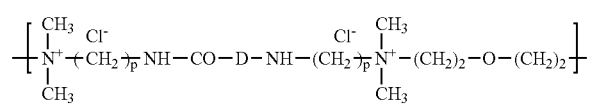
(VI)

wherein p represents an integer ranging from 1 to 6 approximately, D is zero or represents a group —$(CH_2)_r$—CO— wherein r represents a number equal to 4 or 7; and (e) vinylpyrrolidone copolymers containing cationic units.

39. A composition according to claim 1 in the form of a liquid, a shampoo, a cream, or a gel.

40. A composition according to claim 39 in the form of a shampoo.

* * * * *

UNITED STATES PATENT AND TRADEMARK OFFICE
CERTIFICATE OF CORRECTION

PATENT NO. : 7,485,157 B2
APPLICATION NO. : 11/727834
DATED : February 3, 2009
INVENTOR(S) : Christine Rondeau It is certified that error appears in the above-identified patent and that said Letters Patent is hereby corrected as shown below:

In claim 1, column 25, line 12, "formulae" should read --formula--.

In claim 1, column 25, line 53, "also represents" should read --also represent--.

In claim 5, column 30, following structure (I43), ",; and" should read --, and--.

In claim 5, column 30, following structure (I51), ",." should read --.--.

In claim 13, column 32, lines 5-6, "methacryloyloxyethyl-trimethylammonium" should read --methacryloyloxyethyltrimethylammonium--.

In claim 13, column 32, lines 6-7, "methacryloyloxyethyldimethyl-acetylammonium." should read --methacryloyloxyethyldimethylacetylammonium.--.

In claim 30, column 33, line 45, delete "A represents a group selected from structures below:".

In claim 30, column 34, line 43, "formulae" should read --formula--.

In claim 30, column 35, line 24, "also represents" should read --also represent--.

In claim 35, column 37, line 1, delete "A represents a group selected from structures below:".

In claim 35, column 37, line 60, "formulae" should read --formula--.

In claim 35, column 38, line 37, "also represents" should read --also represent--.

In claim 36, column 40, line 17, delete "A represents a group selected from structures below:".

In claim 36, column 41, line 10, "formulae" should read --formula--.

In claim 36, column 41, line 53, "radical:" should read --radical;--.

In claim 36, column 41, line 55, "also represents" should read --also represent--.

In claim 37, column 43, line 40, delete "A represents a group selected from structures below:".

UNITED STATES PATENT AND TRADEMARK OFFICE
CERTIFICATE OF CORRECTION

PATENT NO. : 7,485,157 B2
APPLICATION NO. : 11/727834
DATED : February 3, 2009
INVENTOR(S) : Christine Rondeau It is certified that error appears in the above-identified patent and that said Letters Patent is hereby corrected as shown below:

In claim 37, column 44, line 38, "formulae" should read --formula--.

In claim 37, column 45, line 20, "also represents" should read --also represent--.

In claim 37, column 46, lines 1-5,

" 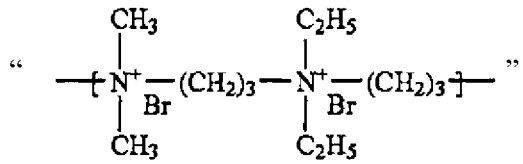 "

should read

-- 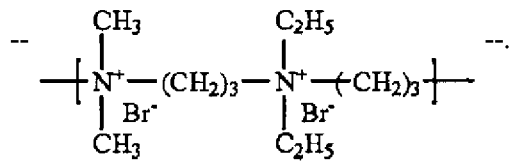 --.

In claim 38, column 46, line 60, delete "A represents a group selected from structures below:".

In claim 38, column 47, line 56, "formulae" should read --formula--.

In claim 38, column 47, line 57, "$R_{13},$ represents" should read --$R_{13}$ represents--.

UNITED STATES PATENT AND TRADEMARK OFFICE
CERTIFICATE OF CORRECTION

PATENT NO. : 7,485,157 B2
APPLICATION NO. : 11/727834
DATED : February 3, 2009
INVENTOR(S) : Christine Rondeau It is certified that error appears in the above-identified patent and that said Letters Patent is hereby corrected as shown below:

In claim 38, column 48, line 34, "also represents" should read --also represent--.

In claim 38, column 48, line 46, "radical:" should read --radical;--.

Signed and Sealed this

Fourteenth Day of April, 2009

JOHN DOLL
*Acting Director of the United States Patent and Trademark Office*